US007618796B2

(12) United States Patent
Tonouchi et al.

(10) Patent No.: US 7,618,796 B2
(45) Date of Patent: Nov. 17, 2009

(54) PEPTIDE-FORMING ENZYME GENE, PEPTIDE-FORMING ENZYME, AND PEPTIDE PRODUCING METHOD

(75) Inventors: Naoto Tonouchi, Kanagawa (JP); Sonoko Suzuki, Kanagawa (JP); Kenzo Yokozeki, Kanagawa (JP); Hiroyuki Nozaki, Kanagawa (JP); Masakazu Sugiyama, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 62 days.

(21) Appl. No.: 11/589,842

(22) Filed: Oct. 31, 2006

(65) Prior Publication Data
US 2007/0048838 A1    Mar. 1, 2007

Related U.S. Application Data

(60) Division of application No. 10/763,249, filed on Jan. 26, 2004, now Pat. No. 7,288,388, which is a continuation of application No. PCT/JP02/07635, filed on Jul. 26, 2002.

(30) Foreign Application Priority Data

Jul. 26, 2001  (JP)  ............................. 2001-226568
Oct. 5, 2001   (JP)  ............................. 2001-310547

(51) Int. Cl.
    *C12P 21/02*    (2006.01)
(52) U.S. Cl. ........................ 435/68.1; 435/212
(58) Field of Classification Search ............ None
    See application file for complete search history.

(56) References Cited

U.S. PATENT DOCUMENTS

| 6,380,370 B1 | 4/2002 | Doucette-Stamm et al. |
| 2005/0148048 A1 | 7/2005 | Hashimoto et al. |

FOREIGN PATENT DOCUMENTS

| EP | 1108790 | 6/2001 |
| JP | 03-013391 | 1/1991 |
| JP | 3-133391 | 6/1991 |
| JP | 6-38769 | 2/1994 |
| JP | 9-503642 | 4/1997 |
| JP | 9-121860 | 5/1997 |
| RU | 2 028 380 | 2/1995 |
| WO | 94/26882 | 11/1994 |
| WO | 01/00842 | 1/2001 |
| WO | WO 03/010189 | 2/2003 |

OTHER PUBLICATIONS

Corynebacterium—Wikipedia printout, Jul. 11, 2008.*
Bacillus—Wikipedia printout, Jul. 11, 2008.*
Pseudomonas—Wikipedia printout, Jul. 11, 2008.*
T. Ohshiro, et al., "Manufacture of Proline-Containing Dipeptides with Proline Iminopeptidase," Database Accession No. 116:5313, Jan. 11, 1992, XP002470964.
T. Ohshiro,e t al., "Enzymatic Peptide Synthesis by Proline Iminopeptidase," Biotechnology Letters, vol. 14, No. 3, Mar. 1992, pp. 175-178, XP002470963.
"Prolyl Aminopeptidase," Database Brenda, Feb. 27, 2008, Database Accession No. EC 3.4.11.5, XP002470965.
M. Gobbetti, et al., "Purification and characterization of an extracellular proline iminopeptidase from Corynebacterium variabilis NCDO 2101," Journal of Applied Microbiology, 90, 2001, pp 449-456.
Database UniProt 'Online! Mar. 1, 2001, "Prolyl aminopeptides." XP002332728, Accession No. Q9HUA3.
Database EMBL 'Online! Nov. 25, 2997, "Pseudomonas putida inducible histidine transporter (hulT), imidazolone propionate hydrolase (hutl), and N-formylglutamate amidohydrolase (hutG) genes,complete cds; and proline iminopeptidase (pipl) gene, partial cds." XP002332729, Accession No. AF032970.
Database EMBL "Online! Sep. 1, 2000, Pseudomonas aeruginosa PA01, section 482 of 529 of the complete geonome." XP002332730, Accession No. AE004921.
Bergmeyer H. U. "Ed!: Methods of Enzymatic Analysis" 1984, Verlag Chemie, Weinheim, XP002332727, ISNB: 3-527-26045-5, Third edition, vol. V; Enzymes 3: Peptidases, Proteinases and their inhibitors, chapter 1.1.1 "Introduction"; pp. 2-5.
Database Brenda Jun. 17, 2005, XP002332731, EC No. 3.4.13.18 Commentary.
C. K. Stover, et al. "Complete Genome Sequence of Pseudomonas Aeruginosa PA01, an Opportunistic Pathogen", Nature, vol. 406, No. 6799, Aug. 31, 2000, pp. 959-964.
Office Action dated May 8, 2009 w/English translation. Chinese Office Action on Application 2006101003905.
A. Kitazono, et al., "Cloning, Sequencing, and High Expresion of the Proline Iminopeptidase Gene from Bacillus coagulans", Journal of Bacteriology, Dec. 1992, pp. 7919-7925.
B. Fricke, et al., "Periplasmic Aminopeptidases in Acinetobacter calcoaceticus and Pseudomonas aeruginosa", J. Basic Microbiol., vol. 33, Nov. 5, 1993, pp. 291-299.

* cited by examiner

*Primary Examiner*—Rebecca Prouty
(74) *Attorney, Agent, or Firm*—Oblon, Spivak, McClelland, Maier & Neustadt, L.L.P.

(57) ABSTRACT

The present invention provides a method for producing dipeptide using inexpensively acquirable starting materials by an industrially advantageous and simple pathway. Dipeptide is produced from L-amino acid ester and L-amino acid using a culture of microbes having the ability to produce a dipeptide from an L-amino acid ester and an L-amino acid, using microbial cells isolated from the culture, or a treated microbial cell product of the microbe.

13 Claims, 1 Drawing Sheet

```
                        SEQUENCE LISTING

<160> NUMBER OF SEQ ID NOS: 17

<210> SEQ ID NO 1
<211> LENGTH: 30
<212> TYPE: PRT
<213> ORGANISM: Corynebacterium glutamicum
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 1

Thr Lys Thr Leu Gly Ser Leu Gln Leu Glu Glu Ile Thr Leu Thr Leu
1               5                   10                  15

Pro Leu Thr Glu Asp Val Ala Asp Glu Xaa Arg Xaa Glu Xaa
            20                  25                  30

<210> SEQ ID NO 2
<211> LENGTH: 26
```

```
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is a, c, g, or t

<400> SEQUENCE: 2
gghwsnytbc arytbgarga ratyac                                              26

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
carytbgarg aratyacbyt bacbytb                                             27

<210> SEQ ID NO 4
<211> LENGTH: 1307
<212> TYPE: DNA
<213> ORGANISM: Corynebacterium glutamicum
<220> FEATURE:
<221> NAME/KEY: CDS
<222> LOCATION: (57)..(1295)

<400> SEQUENCE: 4
```

| | | | | | | | | | | | | | | | | |
|---|---|---|---|---|---|---|---|---|---|---|---|---|---|---|---|---|
| ggcgagctcg ggcagtggtg ggggtggtgt ccacccctgc gcgtaacctg ggaagc | | | | | | | | | | | | | | | atg Met 1 | | 59 |
| act Thr | aaa Lys | aca Thr | ctt Leu | ggt Gly 5 | tcc Ser | ctt Leu | caa Gln | ctt Leu | gaa Glu 10 | gaa Glu | att Ile | acc Thr | ttg Leu | acg Thr 15 | ctc Leu | 107 |
| cct Pro | ctg Leu | act Thr | gaa Glu 20 | gat Asp | gtg Val | gcc Ala | gat Asp | gaa Glu 25 | cgc Arg | acc Thr | att Ile | gat Asp | gtg Val 30 | ttc Phe | gca Ala | 155 |
| cgc Arg | att Ile | gcc Ala 35 | aca Thr | cgc Arg | gtc Val | ggt Gly | ggg Gly 40 | gaa Glu | gac Asp | ctt Leu | cca Pro | tat Tyr 45 | tta Leu | gta Val | ttc Phe | 203 |
| ctg Leu | cag Gln 50 | ggt Gly | ggg Gly | cct Pro | ggc Gly | aat Asn 55 | gaa Glu | gct Ala | cca Pro | cgt Arg | cca Pro 60 | agc Ser | ctt Leu | aat Asn | ccc Pro 65 | 251 |
| ctc Leu | aac Asn | ccc Pro | aat Asn | tgg Trp 70 | ttg Leu | ggc Gly | gtg Val | gcc Ala | ttg Leu 75 | gag Glu | gaa Glu | tac Tyr | cgc Arg | gtg Val 80 | gtc Val | 299 |
| atg Met | ttg Leu | gat Asp | caa Gln 85 | cgt Arg | ggc Gly | acc Thr | ggc Gly | cgt Arg 90 | tcc Ser | acc Thr | cca Pro | gtg Val | ggt Gly 95 | aat Asn | gat Asp | 347 |
| att Ile | ttg Leu | gaa Glu 100 | aaa Lys | ccc Pro | aca Thr | gca Ala | gaa Glu 105 | gta Val | gtg Val | gag Glu | tac Tyr | tta Leu 110 | tcc Ser | cac His | ctg Leu | 395 |
| cgc Arg | gca Ala 115 | gat Asp | ggc Gly | att Ile | gtg Val | cga Arg 120 | gat Asp | gct Ala | gaa Glu | gcc Ala | ctg Leu 125 | cgt Arg | aag Lys | cat His | ttg Leu | 443 |
| ggt Gly 130 | gtg Val | aat Asn | cag Gln | tgg Trp | aac Asn 135 | ctt Leu | tta Leu | ggc Gly | cag Gln | tcc Ser 140 | ttc Phe | gga Gly | ggt Gly | ttc Phe | acc Thr 145 | 491 |
| acc Thr | ctg Leu | cat His | tac Tyr | ttg Leu 150 | tcc Ser | cgg Arg | cac His | gcc Ala | gat Asp 155 | tcc Ser | ttg Leu | gac Asp | aac Asn | gtg Val 160 | ttt Phe | 539 |

```
att acc ggc ggt ctc agc gct att gat cgc cca gca gaa gac gtg tat      587
Ile Thr Gly Gly Leu Ser Ala Ile Asp Arg Pro Ala Glu Asp Val Tyr
            165                 170                 175 gcc aac tgt tac aac cgc atg cgc cga aac tct gag gaa ttc tac cgt      635
Ala Asn Cys Tyr Asn Arg Met Arg Arg Asn Ser Glu Glu Phe Tyr Arg
        180                 185                 190 cgc ttc ccg caa tta cgg gaa act ttc cga ggg ttg gtt aat cgt gct      683
Arg Phe Pro Gln Leu Arg Glu Thr Phe Arg Gly Leu Val Asn Arg Ala
    195                 200                 205 cgc gcc ggg gag att gtg ctt ccc acc ggc gaa gtt gtg tca gaa acc      731
Arg Ala Gly Glu Ile Val Leu Pro Thr Gly Glu Val Val Ser Glu Thr
210                 215                 220                 225 agg ctg cga tcc ctt ggt cac ttg ttg ggt agc aat gac ggc tgg ttt      779
Arg Leu Arg Ser Leu Gly His Leu Leu Gly Ser Asn Asp Gly Trp Phe
                230                 235                 240 gat ctg tac aac ctg ctg gaa tta gat ccc acc tcc aac gct ttt gtc      827
Asp Leu Tyr Asn Leu Leu Glu Leu Asp Pro Thr Ser Asn Ala Phe Val
            245                 250                 255 cat gac ctg gca gga ctt ttg cct ttc ggc aac cgc aac cca att tat      875
His Asp Leu Ala Gly Leu Leu Pro Phe Gly Asn Arg Asn Pro Ile Tyr
        260                 265                 270 tac gtg ctc cat gag tcc tct tac gcc gac ggt gtg gtg aca aat tgg      923
Tyr Val Leu His Glu Ser Ser Tyr Ala Asp Gly Val Val Thr Asn Trp
    275                 280                 285 gca gca gag cgt gtg ctt cca gag gat ttc cgc gag gat cca aca ctg      971
Ala Ala Glu Arg Val Leu Pro Glu Asp Phe Arg Glu Asp Pro Thr Leu
290                 295                 300                 305 ctc acc ggt gag cac gtg ttc cag gag tgg aca gac acc gtg ccg tcg     1019
Leu Thr Gly Glu His Val Phe Gln Glu Trp Thr Asp Thr Val Pro Ser
                310                 315                 320 ctc aag ccg tgg aag gac gtt gcc ctg gca ttg gct cag cag gaa tgg     1067
Leu Lys Pro Trp Lys Asp Val Ala Leu Ala Leu Ala Gln Gln Glu Trp
            325                 330                 335 ccc aag ctt tat gat gcg aag gca ttg gaa aac tca cag gcc aag ggc     1115
Pro Lys Leu Tyr Asp Ala Lys Ala Leu Glu Asn Ser Gln Ala Lys Gly
        340                 345                 350 gct gca gca gtg tat ghc aat gac gtt ttc gtc cca gtg gat tac tct     1163
Ala Ala Ala Val Tyr Xaa Asn Asp Val Phe Val Pro Val Asp Tyr Ser
    355                 360                 365 ctg gaa acc gca caa cac ctg ccc ggt gtg cag ctg ttt atc acc agc     1211
Leu Glu Thr Ala Gln His Leu Pro Gly Val Gln Leu Phe Ile Thr Ser
370                 375                 380                 385 cag cat gaa cac aat gga ctt cgt gcc agc tca ggc gca gta ctg rag     1259
Gln His Glu His Asn Gly Leu Arg Ala Ser Ser Gly Ala Val Leu Xaa
                390                 395                 400 cac ctt ttc gat ctg gcc cac ggc cga gag gta cgc tgagggcccc cg       1307
His Leu Phe Asp Leu Ala His Gly Arg Glu Val Arg
            405                 410

<210> SEQ ID NO 5
<211> LENGTH: 413
<212> TYPE: PRT
<213> ORGANISM: Corynebacterium glutamicum
<220> FEATURE:
<221> NAME/KEY: misc_feature
<222> LOCATION: (359)..(359)
<223> OTHER INFORMATION: The 'Xaa' at location 359 stands for Asp, Ala,
      or Val.
<220> FEATURE:
<221> NAME/KEY: misc_feature
<222> LOCATION: (401)..(401)
<223> OTHER INFORMATION: The 'Xaa' at location 401 stands for Glu, or
```

Lys.

<400> SEQUENCE: 5

```
Met Thr Lys Thr Leu Gly Ser Leu Gln Leu Glu Glu Ile Thr Leu Thr
1               5                   10                  15

Leu Pro Leu Thr Glu Asp Val Ala Asp Glu Arg Thr Ile Asp Val Phe
            20                  25                  30

Ala Arg Ile Ala Thr Arg Val Gly Gly Glu Asp Leu Pro Tyr Leu Val
        35                  40                  45

Phe Leu Gln Gly Gly Pro Gly Asn Glu Ala Pro Arg Pro Ser Leu Asn
    50                  55                  60

Pro Leu Asn Pro Asn Trp Leu Gly Val Ala Leu Glu Glu Tyr Arg Val
65                  70                  75                  80

Val Met Leu Asp Gln Arg Gly Thr Gly Arg Ser Thr Pro Val Gly Asn
                85                  90                  95

Asp Ile Leu Glu Lys Pro Thr Ala Glu Val Val Glu Tyr Leu Ser His
            100                 105                 110

Leu Arg Ala Asp Gly Ile Val Arg Asp Ala Glu Ala Leu Arg Lys His
        115                 120                 125

Leu Gly Val Asn Gln Trp Asn Leu Leu Gly Gln Ser Phe Gly Gly Phe
    130                 135                 140

Thr Thr Leu His Tyr Leu Ser Arg His Ala Asp Ser Leu Asp Asn Val
145                 150                 155                 160

Phe Ile Thr Gly Gly Leu Ser Ala Ile Asp Arg Pro Ala Glu Asp Val
                165                 170                 175

Tyr Ala Asn Cys Tyr Asn Arg Met Arg Arg Asn Ser Glu Glu Phe Tyr
            180                 185                 190

Arg Arg Phe Pro Gln Leu Arg Glu Thr Phe Arg Gly Leu Val Asn Arg
        195                 200                 205

Ala Arg Ala Gly Glu Ile Val Leu Pro Thr Gly Glu Val Val Ser Glu
    210                 215                 220

Thr Arg Leu Arg Ser Leu Gly His Leu Leu Gly Ser Asn Asp Gly Trp
225                 230                 235                 240

Phe Asp Leu Tyr Asn Leu Leu Glu Leu Asp Pro Thr Ser Asn Ala Phe
                245                 250                 255

Val His Asp Leu Ala Gly Leu Leu Pro Phe Gly Asn Arg Asn Pro Ile
            260                 265                 270

Tyr Tyr Val Leu His Glu Ser Ser Tyr Ala Asp Gly Val Val Thr Asn
        275                 280                 285

Trp Ala Ala Glu Arg Val Leu Pro Glu Asp Phe Arg Glu Asp Pro Thr
    290                 295                 300

Leu Leu Thr Gly Glu His Val Phe Gln Glu Trp Thr Asp Thr Val Pro
305                 310                 315                 320

Ser Leu Lys Pro Trp Lys Asp Val Ala Leu Ala Leu Ala Gln Gln Glu
                325                 330                 335

Trp Pro Lys Leu Tyr Asp Ala Lys Ala Leu Glu Asn Ser Gln Ala Lys
            340                 345                 350

Gly Ala Ala Ala Val Tyr Xaa Asn Asp Val Phe Val Pro Val Asp Tyr
        355                 360                 365

Ser Leu Glu Thr Ala Gln His Leu Pro Gly Val Gln Leu Phe Ile Thr
    370                 375                 380

Ser Gln His Glu His Asn Gly Leu Arg Ala Ser Ser Gly Ala Val Leu
385                 390                 395                 400
```

Xaa His Leu Phe Asp Leu Ala His Gly Arg Glu Val Arg
            405                 410

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
ggcgagctcg ggcagtggtg ggggtggtgt                              30

<210> SEQ ID NO 7
<211> LENGTH: 30
<212> TYPE: DNA
<213> ORGANISM: Artificial Sequence
<220> FEATURE:
<223> OTHER INFORMATION: Synthetic DNA

<400> SEQUENCE: 7
cgggggccct cagcgtacct ctcggccgtg                              30

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
ggcgagctca tgactaaaac acttggttcc                              30

<210> SEQ ID NO 9
<211> LENGTH: 25
<212> TYPE: DNA
<213> ORGANISM: Artificial Sequence
<220> FEATURE:
<223> OTHER INFORMATION: Synthetic DNA

<400> SEQUENCE: 9
ggcggatccg gtgctcaaag cgcaa                                   25

<210> SEQ ID NO 10
<211> LENGTH: 25
<212> TYPE: DNA
<213> ORGANISM: Artificial Sequence
<220> FEATURE:
<223> OTHER INFORMATION: Synthetic DNA

<400> SEQUENCE: 10
ggcggatcag gtcgccgcgt tcttc                                   25

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA

<400> SEQUENCE: 11
cacgcgctgc agcaaacccc tcat                                    24

<210> SEQ ID NO 12
<211> LENGTH: 26
<212> TYPE: DNA

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 12
cccgaattct tacggagcgc gcaatg                                          26

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 13
cggggatccc ttcatgcttc ttcagg                                          26

<210> SEQ ID NO 14
<211> LENGTH: 2078
<212> TYPE: DNA
<213> ORGANISM: Pseudomonas putida
<220> FEATURE:
<221> NAME/KEY: CDS
<222> LOCATION: (486)..(1496)

<400> SEQUENCE: 14

```
agatctggcg cccgtatcac ggcacccttc ggcgcgaact ggaccggttg cgcgagcagt      60
ttggctatgc cctgttgtgg gatgcccact cgatccgctc gcacatcccg cacctgttcg     120
atggcaagtt gccggacttc aacctgggta ccttcaatgg cgccagctgc gatccggtgc     180
tggccgagcg gttgcagggc gtgtgcgccg aagcgacagg ttacagtcat gtgttgaatg     240
gtcggttcaa aggcggacac atcacccggc actatggtga ccccgcgaag catatccatg     300
cggtgcagct ggagttggcg caaagcacgt acatggagga aaccgagccg tttacctacc     360
gggaagacct ggcgcaaccg acgcaggtgg ttctgaagca gcttttgcaa cgcgctgctgg    420 cttgggggc agaacgatac cagcgttgag tggaagaggc ggtgctcaaa gcgcaattca     480 ggttt atg atg ccc aac ggc agt caa tat cct cac acg gag tgc gca atg    530
      Met Met Pro Asn Gly Ser Gln Tyr Pro His Thr Glu Cys Ala Met
        1               5                  10                 15 cag acc ctc tac ccg cag atc aaa ccc tac gcc cgg cac gat ctg gcc     578
Gln Thr Leu Tyr Pro Gln Ile Lys Pro Tyr Ala Arg His Asp Leu Ala
             20                  25                  30 gtg gaa gcg ccg cat gtg ctg tat gtc gat gaa agc ggc tcg ccg gaa     626
Val Glu Ala Pro His Val Leu Tyr Val Asp Glu Ser Gly Ser Pro Glu
         35                  40                  45 ggt ctg ccc gtg gta ttc atc cac ggt ggc ccg ggt gct ggc tgc gac     674
Gly Leu Pro Val Val Phe Ile His Gly Gly Pro Gly Ala Gly Cys Asp
     50                  55                  60 gcc cag agc cgt tgc tac ttt gac ccc aac ctg tac cgc atc atc acc     722
Ala Gln Ser Arg Cys Tyr Phe Asp Pro Asn Leu Tyr Arg Ile Ile Thr
 65                  70                  75 ttc gac cag cgc ggc tgt ggc cgc tcc acg ccc cat gcc agc ctg gag     770
Phe Asp Gln Arg Gly Cys Gly Arg Ser Thr Pro His Ala Ser Leu Glu
 80                  85                  90                  95 aac aac aca acc tgg cac ctg gtc gag gac ctg gag cgc atc cgc gag     818
Asn Asn Thr Thr Trp His Leu Val Glu Asp Leu Glu Arg Ile Arg Glu
                 100                 105                 110 cac ctg ggc atc gac aaa tgg gtg ctg ttc ggc ggc tcg tgg ggt tcg     866
His Leu Gly Ile Asp Lys Trp Val Leu Phe Gly Gly Ser Trp Gly Ser
             115                 120                 125
```

```
acc ctg gcc ctg gcc tac gcc cag acc cac ccc gag cgt gtg cat ggg      914
Thr Leu Ala Leu Ala Tyr Ala Gln Thr His Pro Glu Arg Val His Gly
            130                 135                 140 ctg atc ctg cgg ggc atc ttc ctg tgc cgg ccg cag gag atc gag tgg      962
Leu Ile Leu Arg Gly Ile Phe Leu Cys Arg Pro Gln Glu Ile Glu Trp
145                 150                 155 ttc tac cag gag ggc gcc agc cgc ctg ttc ccc gac tac tgg cag gac     1010
Phe Tyr Gln Glu Gly Ala Ser Arg Leu Phe Pro Asp Tyr Trp Gln Asp
160                 165                 170                 175 tac atc gcg ccg att ccg ccg gaa gaa cgc ggc gac ctg gtc aag gcc     1058
Tyr Ile Ala Pro Ile Pro Pro Glu Glu Arg Gly Asp Leu Val Lys Ala
                180                 185                 190 ttc cac aag cgc ctc acc ggt aac gat cag att gcc cag atg cac gcc     1106
Phe His Lys Arg Leu Thr Gly Asn Asp Gln Ile Ala Gln Met His Ala
            195                 200                 205 gcc aag gcg tgg tct acc tgg gag ggc cgt acc gcc acc ctg cgc ccg     1154
Ala Lys Ala Trp Ser Thr Trp Glu Gly Arg Thr Ala Thr Leu Arg Pro
        210                 215                 220 aac ccg ctg gtg gtc gac cgc ttc tcc gag ccg cag cgg gcg ctg tcg     1202
Asn Pro Leu Val Val Asp Arg Phe Ser Glu Pro Gln Arg Ala Leu Ser
225                 230                 235 atc gcc cgg atc gag tgc cac tac ttc atg aac aac gcc ttc ctc gaa     1250
Ile Ala Arg Ile Glu Cys His Tyr Phe Met Asn Asn Ala Phe Leu Glu
240                 245                 250                 255 ccg gac cag ttg atc cgc gac ctg ccg aag atc gcc cac ctg cca gcg     1298
Pro Asp Gln Leu Ile Arg Asp Leu Pro Lys Ile Ala His Leu Pro Ala
                260                 265                 270 gtg atc gtg cac ggt cgc tat gac gtg atc tgt ccg ctg gac aac gcc     1346
Val Ile Val His Gly Arg Tyr Asp Val Ile Cys Pro Leu Asp Asn Ala
            275                 280                 285 tgg gcc ctg cac cag gcc tgg ccg aac agc gaa ctg aag gtg atc cgc     1394
Trp Ala Leu His Gln Ala Trp Pro Asn Ser Glu Leu Lys Val Ile Arg
        290                 295                 300 gac gcc ggc cac gcc gcg tcc gag ccg ggc atc acc gat gcc ctg gtg     1442
Asp Ala Gly His Ala Ala Ser Glu Pro Gly Ile Thr Asp Ala Leu Val
305                 310                 315 cgg gca gcc gac cag atg gcc cgg cgc ctg ctc gac ctg ccc ctg gaa     1490
Arg Ala Ala Asp Gln Met Ala Arg Arg Leu Leu Asp Leu Pro Leu Glu
320                 325                 330                 335 gaa gca tgagggttt gctgcagcgc gtgcgcggtg cgcgggttga agtggcgggg       1546
Glu Ala caggtggttg gcgcgatcga ccagggtttg ctggtgctgg tggccgtcga gcctgaagat   1606
tcccgcgagc aggccgataa gctgttgcac aagctgctga actaccgtgt attcagcgat   1666
gagcacggca agatgaacct gtcgctcaag gatgtcgggg gtggtttgtt gctggtgtcg   1726
cagttcacct tggcggcgga cacccgcaac ggcatgcgtc cgagcttctc gacggcagcg   1786
ccgccggccc tcgggctga attgttcgac tatcttttgc agcaagcgaa cgccagcat    1846 gccgacgtgg cgagcgggca attcggggca gacatgcagg tgcatctggt caatgatggc   1906
cccgtaacat ttatgttaca aatatgaggt caaaaaaccc tttgtttata ggaaaacaag   1966
gggttttgta cgataaatag ttgttccagc ctgatgcgtt gtcacgcgac ctgctggata   2026
atcgcgcgct gcatggacct gcgttcgcag gttcgtttca ctctgactcg ag          2078

<210> SEQ ID NO 15
<211> LENGTH: 337
<212> TYPE: PRT
<213> ORGANISM: Pseudomonas putida
```

<400> SEQUENCE: 15

| | | | | | | | | | | | | | | | |
|---|---|---|---|---|---|---|---|---|---|---|---|---|---|---|---|
| Met | Met | Pro | Asn | Gly | Ser | Gln | Tyr | Pro | His | Thr | Glu | Cys | Ala | Met | Gln |
| 1 | | | | 5 | | | | | 10 | | | | | 15 | |

| Thr | Leu | Tyr | Pro | Gln | Ile | Lys | Pro | Tyr | Ala | Arg | His | Asp | Leu | Ala | Val |
|---|---|---|---|---|---|---|---|---|---|---|---|---|---|---|---|
| | | | 20 | | | | | 25 | | | | | 30 | | |

| Glu | Ala | Pro | His | Val | Leu | Tyr | Val | Asp | Glu | Ser | Gly | Ser | Pro | Glu | Gly |
|---|---|---|---|---|---|---|---|---|---|---|---|---|---|---|---|
| | | | 35 | | | | | 40 | | | | | 45 | | |

| Leu | Pro | Val | Val | Phe | Ile | His | Gly | Gly | Pro | Gly | Ala | Gly | Cys | Asp | Ala |
|---|---|---|---|---|---|---|---|---|---|---|---|---|---|---|---|
| | 50 | | | | | 55 | | | | | 60 | | | | |

| Gln | Ser | Arg | Cys | Tyr | Phe | Asp | Pro | Asn | Leu | Tyr | Arg | Ile | Ile | Thr | Phe |
|---|---|---|---|---|---|---|---|---|---|---|---|---|---|---|---|
| 65 | | | | | 70 | | | | | 75 | | | | | 80 |

| Asp | Gln | Arg | Gly | Cys | Gly | Arg | Ser | Thr | Pro | His | Ala | Ser | Leu | Glu | Asn |
|---|---|---|---|---|---|---|---|---|---|---|---|---|---|---|---|
| | | | | 85 | | | | | 90 | | | | | 95 | |

| Asn | Thr | Thr | Trp | His | Leu | Val | Glu | Asp | Leu | Glu | Arg | Ile | Arg | Glu | His |
|---|---|---|---|---|---|---|---|---|---|---|---|---|---|---|---|
| | | | 100 | | | | | 105 | | | | | 110 | | |

| Leu | Gly | Ile | Asp | Lys | Trp | Val | Leu | Phe | Gly | Gly | Ser | Trp | Gly | Ser | Thr |
|---|---|---|---|---|---|---|---|---|---|---|---|---|---|---|---|
| | | | 115 | | | | | 120 | | | | | 125 | | |

| Leu | Ala | Leu | Ala | Tyr | Ala | Gln | Thr | His | Pro | Glu | Arg | Val | His | Gly | Leu |
|---|---|---|---|---|---|---|---|---|---|---|---|---|---|---|---|
| | 130 | | | | | 135 | | | | | 140 | | | | |

| Ile | Leu | Arg | Gly | Ile | Phe | Leu | Cys | Arg | Pro | Gln | Glu | Ile | Glu | Trp | Phe |
|---|---|---|---|---|---|---|---|---|---|---|---|---|---|---|---|
| 145 | | | | | 150 | | | | | 155 | | | | | 160 |

| Tyr | Gln | Glu | Gly | Ala | Ser | Arg | Leu | Phe | Pro | Asp | Tyr | Trp | Gln | Asp | Tyr |
|---|---|---|---|---|---|---|---|---|---|---|---|---|---|---|---|
| | | | | 165 | | | | | 170 | | | | | 175 | |

| Ile | Ala | Pro | Ile | Pro | Pro | Glu | Glu | Arg | Gly | Asp | Leu | Val | Lys | Ala | Phe |
|---|---|---|---|---|---|---|---|---|---|---|---|---|---|---|---|
| | | | 180 | | | | | 185 | | | | | 190 | | |

| His | Lys | Arg | Leu | Thr | Gly | Asn | Asp | Gln | Ile | Ala | Gln | Met | His | Ala | Ala |
|---|---|---|---|---|---|---|---|---|---|---|---|---|---|---|---|
| | | | 195 | | | | | 200 | | | | | 205 | | |

| Lys | Ala | Trp | Ser | Thr | Trp | Glu | Gly | Arg | Thr | Ala | Thr | Leu | Arg | Pro | Asn |
|---|---|---|---|---|---|---|---|---|---|---|---|---|---|---|---|
| | 210 | | | | | 215 | | | | | 220 | | | | |

| Pro | Leu | Val | Val | Asp | Arg | Phe | Ser | Glu | Pro | Gln | Arg | Ala | Leu | Ser | Ile |
|---|---|---|---|---|---|---|---|---|---|---|---|---|---|---|---|
| 225 | | | | | 230 | | | | | 235 | | | | | 240 |

| Ala | Arg | Ile | Glu | Cys | His | Tyr | Phe | Met | Asn | Asn | Ala | Phe | Leu | Glu | Pro |
|---|---|---|---|---|---|---|---|---|---|---|---|---|---|---|---|
| | | | | 245 | | | | | 250 | | | | | 255 | |

| Asp | Gln | Leu | Ile | Arg | Asp | Leu | Pro | Lys | Ile | Ala | His | Leu | Pro | Ala | Val |
|---|---|---|---|---|---|---|---|---|---|---|---|---|---|---|---|
| | | | 260 | | | | | 265 | | | | | 270 | | |

| Ile | Val | His | Gly | Arg | Tyr | Asp | Val | Ile | Cys | Pro | Leu | Asp | Asn | Ala | Trp |
|---|---|---|---|---|---|---|---|---|---|---|---|---|---|---|---|
| | | 275 | | | | | 280 | | | | | 285 | | | |

| Ala | Leu | His | Gln | Ala | Trp | Pro | Asn | Ser | Glu | Leu | Lys | Val | Ile | Arg | Asp |
|---|---|---|---|---|---|---|---|---|---|---|---|---|---|---|---|
| | 290 | | | | | 295 | | | | | 300 | | | | |

| Ala | Gly | His | Ala | Ala | Ser | Glu | Pro | Gly | Ile | Thr | Asp | Ala | Leu | Val | Arg |
|---|---|---|---|---|---|---|---|---|---|---|---|---|---|---|---|
| 305 | | | | | 310 | | | | | 315 | | | | | 320 |

| Ala | Ala | Asp | Gln | Met | Ala | Arg | Arg | Leu | Leu | Asp | Leu | Pro | Leu | Glu | Glu |
|---|---|---|---|---|---|---|---|---|---|---|---|---|---|---|---|
| | | | | 325 | | | | | 330 | | | | | 335 | |

Ala

<210> SEQ ID NO 16
<211> LENGTH: 1360
<212> TYPE: DNA
<213> ORGANISM: Pseudomonas putida
<220> FEATURE:
<221> NAME/KEY: CDS
<222> LOCATION: (311)..(1279)
<220> FEATURE:
<221> NAME/KEY: misc_feature
<222> LOCATION: (1297)..(1298)
<223> OTHER INFORMATION: n is a, c, g, or t

<400> SEQUENCE: 16

```
ctggaagggt tcttggcgtg gggccagaag cactacacct gagtcaacga ggatcaaaat      60
gtgggagcgg gcttgtcagg tcgccgcatc gccgcgatgg cggtctgtca gttcccaata     120
tgtcgactga tccgccgcta tcgcgagcaa gcccgctccc acacgtggtg cgcgaacctt     180
cctggctgat cactgacaca ggtctaagtc ctcaaggaca tgctcattgc acaattcggg     240
tttatgatgc cagacggcaa aataatagac gtccccccag ggatggaccc gacccccttac    300 ggagcgcgca atg cag act ttg tac ccg cag atc aaa ccc tac gtc cgg        349
              Met Gln Thr Leu Tyr Pro Gln Ile Lys Pro Tyr Val Arg
                1               5                  10 cac gat ctg gcc gtc gat gaa acc cac acg ctg tat gtc gac gaa agt        397
His Asp Leu Ala Val Asp Glu Thr His Thr Leu Tyr Val Asp Glu Ser
         15                  20                  25 ggt tcc ccg caa ggt ttg ccc gtg gtc ttc atc cat ggc ggt ccc ggc        445
Gly Ser Pro Gln Gly Leu Pro Val Val Phe Ile His Gly Gly Pro Gly
 30                  35                  40                  45 gcc ggc tgc gat gcc aat agc cgc tgc tat ttc gat ccg aac ctg tac        493
Ala Gly Cys Asp Ala Asn Ser Arg Cys Tyr Phe Asp Pro Asn Leu Tyr
                 50                  55                  60 cgc atc gtc acc ttt gac cag cgc ggc tgc ggg cgc tcc act ccg cgg        541
Arg Ile Val Thr Phe Asp Gln Arg Gly Cys Gly Arg Ser Thr Pro Arg
             65                  70                  75 gcc agc ctg gaa aac aac acc acc tgg gac ctg gtt gcc gac ctt gag        589
Ala Ser Leu Glu Asn Asn Thr Thr Trp Asp Leu Val Ala Asp Leu Glu
         80                  85                  90 cgc att cgc gag cac ctg ggg att gaa aaa tgg gtg ctg ttc ggt ggt        637
Arg Ile Arg Glu His Leu Gly Ile Glu Lys Trp Val Leu Phe Gly Gly
 95                 100                 105 tcc tgg ggc tcg acc ctg gcc ctg gcc tat gca caa acc cac cct gat        685
Ser Trp Gly Ser Thr Leu Ala Leu Ala Tyr Ala Gln Thr His Pro Asp
110                 115                 120                 125 cgc gtg ctt ggc ctg att gtg cgc ggc atc ttc ctg gcc cgc ccc cag        733
Arg Val Leu Gly Leu Ile Val Arg Gly Ile Phe Leu Ala Arg Pro Gln
                130                 135                 140 gat atc cag tgg ttc tac cag gcc ggc gcg agc cgc ctg ttc ccg gac        781
Asp Ile Gln Trp Phe Tyr Gln Ala Gly Ala Ser Arg Leu Phe Pro Asp
            145                 150                 155 tac tgg cag gac tac atc gcg cca atc ccg gcg gaa gag cgc cac gac        829
Tyr Trp Gln Asp Tyr Ile Ala Pro Ile Pro Ala Glu Glu Arg His Asp
        160                 165                 170 atg atc agc gcc tac cac aag cgc ctg acc ggc aat gac cag atc gcc        877
Met Ile Ser Ala Tyr His Lys Arg Leu Thr Gly Asn Asp Gln Ile Ala
    175                 180                 185 cag atg cat gcc gcc aag gcc tgg tcc acc tgg gaa ggc cgc atg ctc        925
Gln Met His Ala Ala Lys Ala Trp Ser Thr Trp Glu Gly Arg Met Leu
190                 195                 200                 205 ggc ctg tgc ccc agc ccg cag ctg atc gag cgc ttc tcc gag ccc cag        973
Gly Leu Cys Pro Ser Pro Gln Leu Ile Glu Arg Phe Ser Glu Pro Gln
                210                 215                 220 cgc gcg ttg tcg att gcg cgc atc gag tgc cac tac ttc acc aat aac       1021
Arg Ala Leu Ser Ile Ala Arg Ile Glu Cys His Tyr Phe Thr Asn Asn
            225                 230                 235 tcg ttc ctg gag ccc aac cag ctg att cgc gat atg cac aag atc gcc       1069
Ser Phe Leu Glu Pro Asn Gln Leu Ile Arg Asp Met His Lys Ile Ala
        240                 245                 250 cat ctg ccg ggg atc atc gtg cat ggc cgc tac gat atg atc tgc ccg       1117
His Leu Pro Gly Ile Ile Val His Gly Arg Tyr Asp Met Ile Cys Pro
```

```
                255                 260                 265
ctg gat aat gcc tgg gag ctg cac cag gcc tgg ccg aac agt gag ttg    1165
Leu Asp Asn Ala Trp Glu Leu His Gln Ala Trp Pro Asn Ser Glu Leu
270                 275                 280                 285 cag gtg atc cgc gag gcg ggc cac gcg gcg tcc gag ccg ggc atc acc    1213
Gln Val Ile Arg Glu Ala Gly His Ala Ala Ser Glu Pro Gly Ile Thr
                290                 295                 300 gat gcg ctg gtg cgt gcg gcg ggc gat atg gca cga cgc ctg ctt gat    1261
Asp Ala Leu Val Arg Ala Ala Gly Asp Met Ala Arg Arg Leu Leu Asp
            305                 310                 315 ctg ccc cct gaa gaa gca tgaagggcct ttttgccnna cgggtgcgtg           1309
Leu Pro Pro Glu Glu Ala
        320 gcgccgggtc agtggcgggc aagtggtggg cgcgatagac cagggttgca g           1360

<210> SEQ ID NO 17
<211> LENGTH: 323
<212> TYPE: PRT
<213> ORGANISM: Pseudomonas putida

<400> SEQUENCE: 17

Met Gln Thr Leu Tyr Pro Gln Ile Lys Pro Tyr Val Arg His Asp Leu
1               5                   10                  15

Ala Val Asp Glu Thr His Thr Leu Tyr Val Asp Glu Ser Gly Ser Pro
            20                  25                  30

Gln Gly Leu Pro Val Val Phe Ile His Gly Gly Pro Gly Ala Gly Cys
        35                  40                  45

Asp Ala Asn Ser Arg Cys Tyr Phe Asp Pro Asn Leu Tyr Arg Ile Val
    50                  55                  60

Thr Phe Asp Gln Arg Gly Cys Gly Arg Ser Thr Pro Arg Ala Ser Leu
65                  70                  75                  80

Glu Asn Asn Thr Thr Trp Asp Leu Val Ala Asp Leu Glu Arg Ile Arg
                85                  90                  95

Glu His Leu Gly Ile Glu Lys Trp Val Leu Phe Gly Gly Ser Trp Gly
            100                 105                 110

Ser Thr Leu Ala Leu Ala Tyr Ala Gln Thr His Pro Asp Arg Val Leu
        115                 120                 125

Gly Leu Ile Val Arg Gly Ile Phe Leu Ala Arg Pro Gln Asp Ile Gln
    130                 135                 140

Trp Phe Tyr Gln Ala Gly Ala Ser Arg Leu Phe Pro Asp Tyr Trp Gln
145                 150                 155                 160

Asp Tyr Ile Ala Pro Ile Pro Ala Glu Glu Arg His Asp Met Ile Ser
                165                 170                 175

Ala Tyr His Lys Arg Leu Thr Gly Asn Asp Gln Ile Ala Gln Met His
            180                 185                 190

Ala Ala Lys Ala Trp Ser Thr Trp Glu Gly Arg Met Leu Gly Leu Cys
        195                 200                 205

Pro Ser Pro Gln Leu Ile Glu Arg Phe Ser Glu Pro Gln Arg Ala Leu
    210                 215                 220

Ser Ile Ala Arg Ile Glu Cys His Tyr Phe Thr Asn Asn Ser Phe Leu
225                 230                 235                 240

Glu Pro Asn Gln Leu Ile Arg Asp Met His Lys Ile Ala His Leu Pro
                245                 250                 255

Gly Ile Ile Val His Gly Arg Tyr Asp Met Ile Cys Pro Leu Asp Asn
            260                 265                 270
```

```
                                       -continued

Ala Trp Glu Leu His Gln Ala Trp Pro Asn Ser Glu Leu Gln Val Ile
        275                 280                 285

Arg Glu Ala Gly His Ala Ala Ser Glu Pro Gly Ile Thr Asp Ala Leu
        290                 295                 300

Val Arg Ala Ala Gly Asp Met Ala Arg Arg Leu Leu Asp Leu Pro Pro
305                 310                 315                 320

Glu Glu Ala
```

PEPTIDE-FORMING ENZYME GENE, PEPTIDE-FORMING ENZYME, AND PEPTIDE PRODUCING METHOD

CROSS-REFERENCE TO RELATED APPLICATIONS

This application is a Divisional of U.S. Ser. No. 10/763,249, filed on Jan. 26, 2004, now U.S. Pat. No. 7,288,388, which is a Continuation of PCT/JP02/07635, filed on Jul. 26, 2002, which claims priority to: JP2001-226568, filed on Jul. 26, 2001 and JP2001-310547, filed on Oct. 5, 2001.

TECHNICAL FIELD

The present invention relates to a method for producing dipeptide conveniently and economically without going through a complicated synthesis method, and more particularly to a peptide-forming enzyme gene, to a peptide-forming enzyme, and to a method for producing dipeptide using the enzyme.

BACKGROUND ART

Dipeptides are used in the field of pharmaceutical materials and functional foods and various fields. For example, L-alanyl-L-glutamine is used as a component of serum-free media, and is used for infusion components since it has greater stability and higher solubility than L-glutamine.

Chemical synthesis methods, which have been conventionally known as methods of producing dipeptides, are not necessarily simple. Known examples of such methods include a method that uses N-benzyloxycarbonylalanine (hereinafter, "Z-alanine") and protected L-glutamine (see Bull. Chem. Soc. Jpn., 34, 739 (1961), Bull. Chem. Soc. Jpn., 35, 1966 (1962)), a method that uses Z-alanine and protected L-glutamate-γ-methyl ester (see Bull. Chem. Soc. Jpn., 37, 200 (1964)), a method that uses a Z-alanine ester and unprotected glutamic acid (see Japanese Patent Application Laid-Open Publication No. H1-96194), and a method that uses a 2-substituted-propionyl halide as raw material and synthesizes an N-(2-substituted)-propionyl glutamine derivative as an intermediate (see Japanese Patent Application Laid-Open Publication No. H6-234715).

However, in all of these methods, the introduction and elimination of a protecting group or the synthesis of an intermediate is required, so that these production methods have not been sufficiently satisfactory in view of their industrial advantages. Known examples of typical dipeptide production methods using enzymes include a condensation reaction using an N-protected, C-unprotected carboxy component and an N-unprotected, C-protected amine component (Reaction 1), and a substitution reaction using an N-protected, C-protected carboxy component and an N-unprotected, C-protected amine component (Reaction 2). An example of Reaction 1 is a production method of Z-aspartylphenylalanine methyl ester from Z-aspartic acid and phenylalanine methyl ester (see Japanese Patent Application Laid-Open Publication No. S53-92729), while an example of Reaction 2 is a production method of acetylphenylalanylleucine amide from acetylphenylalanine ethyl ester and leucine amide (see Biochemical J., 163, 531 (1977)). There are extremely few examples of research reports that describe methods using N-unprotected, C-protected carboxy components. An example of a substitution reaction using an N-unprotected, C-protected carboxy component and an N-unprotected, C-protected amine component (Reaction 3) is described in Patent WO 90/01555, and example of such a reaction is a production method of arginyl leucine amide from arginine ethyl ester and leucine amide. An example of a substitution reaction using an N-unprotected, C-protected carboxy component and an N-unprotected, C-unprotected amine component (Reaction 4) is described in Patent EP 278787A, and example of such a reaction is a production method of tyrosyl alanine from tyrosine ethyl ester and alanine. Among the methods those that are able to serve as the least expensive production methods are naturally those that fall in the range of Reaction 4 involving the fewest number of protecting groups.

However, the enzyme used in the example of the prior art of the Reaction 4 (see Patent EP 278787A) is a comparatively expensive carboxypeptidase preparation derived from molds and plants, and the dipeptides that were produced contained amino acids that are comparatively highly hydrophobic. For the Reaction 4, there is no known method that uses an enzyme of bacterial or yeast origin, and there has been known no method for producing highly hydrophilic alanylglutamine or alanylasparagine. Under such circumstances, there has been a need for the development of an inexpensive industrial method for the production of such peptides.

On the other hand, proline iminopeptidase is an enzyme that catalyzes a reaction that cleaves an N-terminal proline from a peptide having proline on its N-terminal, and this enzyme is known to exist in numerous species of organisms. For example, it is known to exist in higher animals such as guinea pigs (brain) (see J. Biol. Chem., 258, 6147-6154 (1983)), rats (brain and kidneys) (see Eur. J. Biochem., 190, 509-515 (1990)), higher plants such as apricot seeds (see J. Biochem., 92, 413-421 (1982)), oral cavity spirochetes such as *Trichoderma denticola* (see Infect. Immun., 64, 702-708 (1996), filamentous fungi such as *Penicillium* species (see Japanese Patent Application Laid-Open Publication No. H1-215288), *Basidiomycetes* such as shiitake mushrooms (see Japanese Patent Application Laid-Open Publication No. S58-36387), *Actinomycetes* such as *Streptomyces plicatus* (see Biochem. Biophys. Res. Commun., 184, 1250-1255 (1992), and bacteria such as *Corynebacterium variabilis* (see J. Appl. Microbiol., 90, 449-456 (2001)).

In addition, concerning proline iminopeptidase gene, there have been reported cloning and base sequences of genes of *Arthrobacter nicotiana* (see FEMS Microbiol. Lett., 78, 191-197 (1999)), *Escherichia coli* (see Japanese Patent Application Laid-Open Publication No. H2-113887), *Flavobacterium meningosepticum* (see Arch. Biochem. Biophys., 336, 35-41 (1996)), *Hafnia alvei* (see J. Biochem., 119, 468-474 (1996)), *Lactobacillus delbrueckii* (see Microbiology, 140, 527-535 (1994)), *Bacillus coagulans* source (see J. Bacteriol., 174, 7919-1925 (1994)), *Aeromonas sobria* source (see J. Biochem., 116, 818-825 (1994)), *Xanthomonas campestris* (see Japanese Patent Application Laid-Open Publication No. H9-121860), *Neisseria gonorrhoeae* (see Mol. Microbiol., 9, 1203-1211 (1993), *Propionibacterium freundenreichii* (see Appl. Environ. Micorbiol., 64, 4736-4742 (1998)), *Serratia marcescens* (see J. Biochem., 122, 601-605 (1997)) and *Thermoplasma acidophilum* (see FEBS Lett., 398, 101-105 (1996)).

In addition, base sequences predicted to encode proline iminopeptidase have recently been reported in numerous species of organisms as a result of analyses on the whole genomes of microbes. For example, the whole genome base sequence of *Pseudomonas aeruginosa* has been reported (see Nature, 406, 959 (2000)), and a base sequence was found therein that is predicted to encode proline iminopeptidase.

On the other hand, it has been found that a proline-containing dipeptide is formed when an ester of L-proline or DLproline and an alpha-amino acid are allowed to react using proline iminopeptidase (see Japanese Patent Application Laid-Open Publication No. H3-13391). However, although proline iminopeptidase is an enzyme that catalyzes a reaction that cleaves the N-terminal proline from a peptide having a proline on its N-terminal, and a prolyl amino acid would be naturally considered to be produced from proline ester and amino acid, the synthesis of peptide from an amino acid and amino acid ester other than proline using proline iminopeptidase has been completely unknown. Of course, the synthesis of L-alanyl-L-glutamine from L-alanine ethyl ester hydrochloride and L-glutamine has been also previously unknown. In addition, although the partial base sequence of proline iminopeptidase of *Pseudomonas putida* strain ATCC 12633 was disclosed (AF032970), there has been no study conducted whatsoever on its activity, including its detection.

DISCLOSURE OF THE INVENTION

An object of the present invention is to provide a method for producing a dipeptide by an industrially advantageous and simple pathway using a starting material that can be acquired inexpensively and an enzyme source that can be supplied inexpensively (such as a microbial culture, microbial cells or a treated microbial cell product of a microbe).

As a result of extensive research in consideration of the aforementioned object, the inventors of the present invention have found that proline iminopeptidase has the ability to produce a peptide from an L-amino acid ester and an L-amino acid. In addition, the inventors of the present invention also have cloned and expressed the gene of the enzyme and also clearly demonstrated the broad substrate specificity of the enzyme in peptide production using purified recombinant enzymes, thereby leading to completion of the present invention.

The present invention provides:

[1] A protein (A) or (B):
   (A) a protein having an amino acid sequence described in SEQ ID NO: 5 of the Sequence Listing,
   (B) a protein consisting of an amino acid sequence that includes substitution, deletion, insertion, addition or inversion of one or a plurality of amino acids in the amino acid sequence described in SEQ ID NO: 5 of the Sequence Listing, and has activity to produce a dipeptide from an L-amino acid ester and an L-amino acid.

[2] A protein (C) or (D):
   (C) a protein having an amino acid sequence described in SEQ ID NO: 15 of the Sequence Listing,
   (D) a protein consisting of an amino acid sequence that includes substitution, deletion, insertion, addition or inversion of one or a plurality of amino acids in the amino acid sequence described in SEQ ID NO: 15 of the Sequence Listing, and has activity to produce a dipeptide from an L-amino acid ester and an L-amino acid.

[3] A protein (E) or (F):
   (E) a protein having an amino acid sequence described in SEQ ID NO: 17 of the Sequence Listing,
   (F) a protein consisting of an amino acid sequence that includes substitution, deletion, insertion, addition or inversion of one or a plurality of amino acids in the amino acid sequence described in SEQ ID NO: 17 of the Sequence Listing, and has activity to produce a dipeptide from an L-amino acid ester and an L-amino acid.

[4] A DNA (a) or (b):
   (a) a DNA consisting of a base sequence consisting of bases numbers 57 to 1295 in a base sequence described in SEQ ID NO: 4 of the Sequence Listing,
   (b) a DNA that hybridizes under stringent conditions with a DNA consisting of a base sequence consisting of bases numbers 57 to 1295 in the base sequence described in SEQ ID NO: 4 of the Sequence Listing, and encodes a protein having activity to form a dipeptide from an L-amino acid ester and an L-amino acid.

[5] A DNA (c) or (d):
   (c) a DNA consisting of a base sequence consisting of bases numbers 486 to 1496 in a base sequence described in SEQ ID NO: 14 of the Sequence Listing,
   (d) a DNA that hybridizes under stringent conditions with a DNA consisting of a base sequence consisting of bases numbers 486 to 1496 in the base sequence described in SEQ ID NO: 14 of the Sequence Listing, and encodes a protein having activity to form a dipeptide from an L-amino acid ester and an L-amino acid.

[6] A DNA (e) or (f):
   (e) a DNA consisting of a base sequence consisting of bases numbers 311 to 1279 in a base sequence described in SEQ ID NO: 16 of the Sequence Listing,
   (f) a DNA that hybridizes under stringent conditions with a DNA consisting of a base sequence consisting of bases numbers 311 to 1279 in the base sequence described in SEQ ID NO: 16 of the Sequence Listing, and encodes a protein having activity to form a dipeptide from an L-amino acid ester and an L-amino acid.

[7] The DNA according to any one of [4] to [6] above, wherein the stringent conditions are conditions under which washing is carried out at 60° C. and at a salt concentration equivalent to 1×SSC and 0.1% SDS.

[8] A recombinant DNA comprising incorporated therein the DNA according to any one of [4] to [7] above.

[9] A transformed cell comprising incorporated therein the DNA according to any one of [4] to [7] above in a state where the DNA is able to express a protein encoded thereby.

[10] A method for producing a dipeptide-forming enzyme, comprising: culturing the transformed cells according to [9] above in a medium, and accumulating a protein having activity to produce the dipeptide from an L-amino acid ester and an L-amino acid in the medium and/or in the transformed cells.

[11] A method for producing a dipeptide, comprising: producing a dipeptide from an L-amino acid ester and an L-amino acid using a protein having activity to form the dipeptide from an L-amino acid ester and an L-amino acid that is produced in the transformed cells according to [9] above.

[12] The method for producing a dipeptide according to [11] above, wherein the L-amino acid ester is one or more types selected from the group consisting of an L-alanine ester, a glycine ester, an L-valine ester, an L-isoleucine ester, an L-methionine ester, an L-phenylalanine ester, an L-serine ester, an L-threonine ester, an L-glutamine ester, an L-tyrosine ester, an L-arginine ester, an L-aspartic acid-α-ester, an L-aspartic acid-β-ester, an L-leucine ester, an L-asparagine ester, an L-lysine ester, an L-aspartic-α,β-dimethyl ester and an L-glutamine-γ-ester.

[13] The method for producing a dipeptide according to [11] or [12] above, wherein the L-amino acid is one or more types selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

[14] A method for producing a dipeptide comprising: allowing a protein having proline iminopeptidase activity to act on an L-amino acid ester and an L-amino acid to form the dipeptide.

[15] The method for producing dipeptide according to [14] above, wherein the protein having proline iminopeptidase activity is derived from a microbe belonging to genus *Corynebacterium, Pseudomonas* or *Bacillus*.

[16] The method for producing a dipeptide according to [14] above, wherein the protein having proline iminopeptidase activity is derived from any of *Corynebacterium glutamicum, Pseudomonas putida* and *Bacillus coagulans*.

[17] The method for producing a dipeptide according to any one of [14] to [16] above, wherein the L-amino acid ester is one or more types selected from the group consisting of an L-alanine ester, a glycine ester, an L-valine ester, an L-isoleucine ester, an L-methionine ester, an L-phenylalanine ester, an L-serine ester, an L-threonine ester, an L-glutamine ester, an L-tyrosine ester, an L-arginine ester, an L-aspartic acid-α-ester, an L-aspartic acid-β-ester, an L-leucine ester, an L-asparagine ester, an L-lysine ester, an L-aspartic-α,β-dimethyl ester and an L-glutamine-γ-ester.

[18] The method for producing a dipeptide according to any one of [14] to [17] above, wherein the L-amino acid is one or more types selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

[19] A method for producing a dipeptide, comprising: producing the dipeptide from an amino acid ester and an amino acid using a culture of a microbe belonging to the genus *Corynebacterium, Pseudomonas* or *Bacillus* and having the ability to produce the dipeptide from the amino acid ester and the amino acid, microbial cells isolated from the culture or a treated microbial product of the microbe.

[20] The method for producing a dipeptide according to [19] above, wherein the L-amino acid ester is one or more types selected from the group consisting of an L-alanine ester, a glycine ester, an L-valine ester, an L-isoleucine ester, an L-methionine ester, an L-phenylalanine ester, an L-serine ester, an L-threonine ester, an L-glutamine ester, an L-tyrosine ester, an L-arginine ester, an L-aspartic acid-α-ester, an L-aspartic acid-β-ester, an L-leucine ester, an L-asparagine ester, an L-lysine ester, an L-aspartic-α,β-dimethyl ester and an L-glutamine-γ-ester.

[21] The method for producing a dipeptide according to [19] above, wherein the L-amino acid is one or more types selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

The other objects, features and advantages of the present invention are specifically set forth in or will become apparent from the following detailed descriptions of the invention when read in conjunction with the accompanying drawing.

BEST MODE FOR CARRYING OUT THE INVENTION

Figure 1:
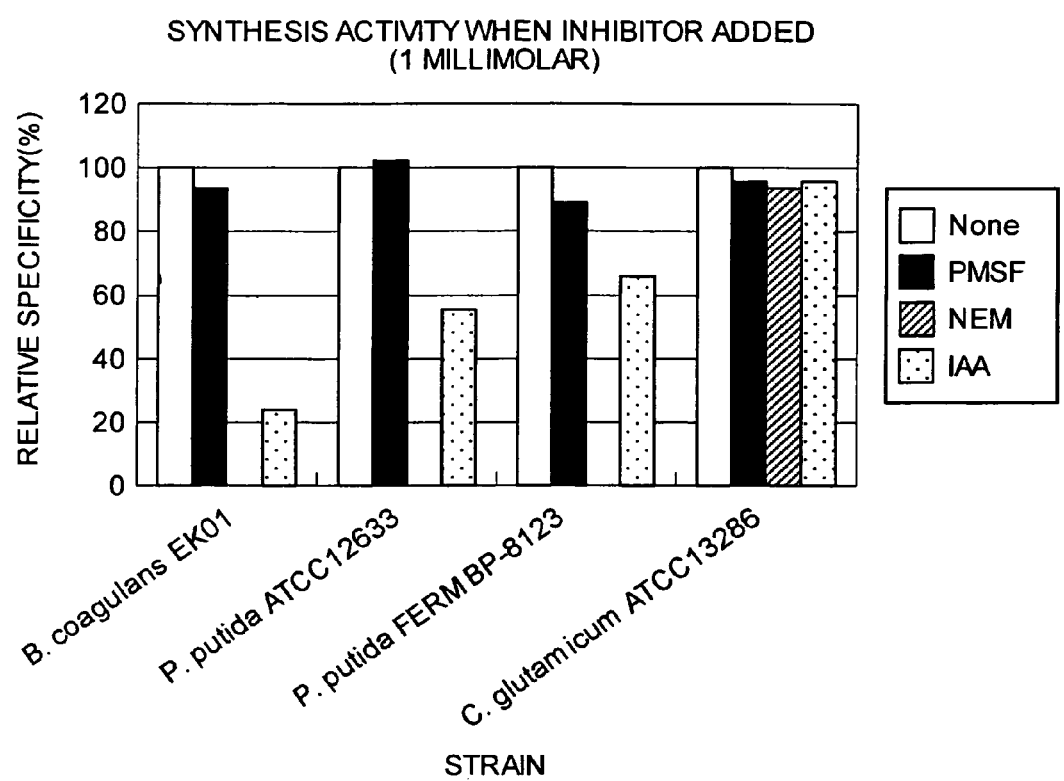
FIG. 1 is a graph illustrating dipeptide-forming activity when an inhibitor is added.

The present invention provides a novel protein having activity to produce a dipeptide from an L-amino acid ester and an L-amino acid, a DNA encoding that protein, and a method for producing a dipeptide using these. The reaction in the dipeptide production method of the present invention is expressed as shown in the reaction scheme below. As exemplified in the following chemical formulae, a "dipeptide" as used herein refers to a peptide polymer having one dipeptide bond.

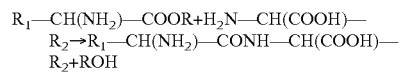

(In the formula, R represents a substituted or non-substituted hydrocarbon chain, $R_1$ represents an amino acid ester side chain, and $R_2$ represents an amino acid side chain.)

Amino acid esters are compounds that can be acquired inexpensively. The method of the present invention, in which starting materials in the form of an amino acid ester and unprotected amino acid are allowed to react in an aqueous solution using bacteria, yeast and so forth as the enzyme source, is a novel dipeptide production method not found conventionally, and is capable of inexpensively providing useful dipeptides for use in pharmaceutical materials and functional foods.

Hereinafter, the present invention will be described in detail in the following order:

[I] Microbes having the ability to produce dipeptides from L-amino acid esters and L-amino acids

[II] Isolation of DNA encoding protein having peptide production activity

[III] Properties of peptide-forming enzyme

[IV] Dipeptide production method.

[I] Microbes Having the Ability to Produce Dipeptides from L-Amino Acid Esters and L-Amino Acids Microbes having the ability to produce dipeptides from L-amino acid esters and L-amino acids can be used without any particular restrictions as the microbe used in the present invention. Examples of microbes having the ability to produce dipeptides from L-amino acid esters and L-amino acids include *Bacillus* species, *Corynebacterium* species and *Pseudomonas* species, and specific examples thereof are indicated below.

*Bacillus subtilis* ATCC 6633

*Bacillus coagulans* EK01 (J. Bacteriol. 174, 7919-7925 (1992))

*Corynebacterium glutamicum* ATCC 13286

*Pseudomonas putida* AJ-2402 FERM BP-8101

*Pseudomonas putida* ATCC 12633

*Pseudomonas putida* AJ-2048 FERM BP-8123

Those strains of microbes listed above that are indicated with ATCC numbers are deposited at the American Type Culture Collection (P.O. Box 1549, Manassas, Va. 20110), and subcultures can be furnished by referring to each number.

Those strains of microbes listed above that are indicated with FERM numbers are deposited at the independent administrative corporation, International Patent Organism Depositary of the National Institute of Advanced Industrial Science and Technology (Chuo Dai-6, 1-1 Higashi 1-Chome, Tsukuba-shi, Ibaraki-ken, 305-8566, Japan) and have been assigned a deposit number. *Pseudomonas putida* strain AJ-2402 was deposited at the independent administrative corporation, International Patent Organism Depositary of the National Institute of Advanced Industrial Science and Technology on Oct. 1, 2001, was assigned the deposit number of FERM P-18544, control of this strain was later transferred to international deposition on Jul. 1, 2002 and assigned the deposit number of FERM BP-8101. Note that FERM BP-8101 (AJ-2402) has been identified as the aforementioned *Pseudomonas putida* based on the following classification experiment. In addition, *Pseudomonas putida* strain AJ-2048 was deposited at the independent administrative corporation, International Patent Organism Depositary of the National Institute of Advanced Industrial Science and Technology on Jul. 22, 2002, and assigned the deposit number of FERM BP-8123.

*Pseudomonas putida* strain FERM BP-8101 is a motile, aconidial rod that was identified as a bacterium belonging to the genus *Pseudomonas* based on the properties of being a Gram negative rod (0.7 to 0.8×1.5 to 2.0 micrometers (μm)) that forms no spore, is motile, forms round, glossy, cream-colored colonies with a completely smooth or undulating border, grows at 30° C., and is catalase positive, oxidase positive and OF test (glucose) negative. Moreover, it was identified as *Pseudomonas putida* based on the physiological properties of being nitrate reduction negative, indole production negative, acid production from glucose negative, arginine dihydrolase positive, urease negative, esculin hydrolysis negative, gelatin hydrolysis negative, β-galactosidase negative, glucose assimilation positive, L-arabinose assimilation negative, D-mannose assimilation positive, D-mannitol assimilation positive, N-acetyl-D-glucosamine assimilation negative, maltose assimilation negative, potassium gluconate assimilation positive, n-capric acid assimilation positive, adipic acid assimilation negative, dl-malic acid assimilation positive, sodium citrate assimilation positive, phenyl acetate assimilation positive, oxidase positive, fluorochrome production on King's B agar medium positive, levan production from sucrose positive, and weak assimilation of sorbitol.

Wild strains or variant strains may be used for these microbes, and recombinant strains and so forth derived by cell fusion, genetic manipulation or other genetic techniques may also be used.

To obtain microbial cells of these microbes, the microbes can be cultured and grown in a suitable medium. There is no particular restriction on the medium used for this purpose so far as it allows the microbes to grow. This medium may be an ordinary medium containing ordinary carbon sources, nitrogen sources, phosphorous sources, sulfur sources, inorganic ions, and organic nutrient sources as necessary.

For example, any carbon source may be used so far as it can be utilized by the aforementioned microbes, and specific examples of which that can be used include sugars such as glucose, fructose, maltose, and amylose, alcohols such as sorbitol, ethanol and glycerol, organic acids such as fumaric acid, citric acid, acetic acid and propionic acid and their salts, hydrocarbons such as paraffin as well as mixtures thereof.

Examples of nitrogen sources that can be used include ammonium salts of inorganic acids such as ammonium sulfate and ammonium chloride, ammonium salts of organic acids such as ammonium fumarate and ammonium citrate, nitrates such as sodium nitrate and potassium nitrate, organic nitrogen compounds such as peptones, yeast extract, meat extract and corn steep liquor as well as mixtures thereof.

In addition, nutrient sources used in ordinary media, such as inorganic salts, trace metals and vitamins, can also be suitably mixed and used.

There is no particular restriction on culturing conditions, and culturing may be carried out, for example, for about 12 to 48 hours while suitably controlling the pH and temperature to a pH range of 5 to 8 and a temperature range of 15 to 40° C. under aerobic conditions.

[II] Isolation of DNA Encoding Protein Having Peptide-Forming Enzyme Activity

[II-1] DNA Isolation

The inventors of the present invention have isolated and determined the sequence of DNA of the present invention that encodes protein having activity to synthesize a dipeptide from an L-amino acid ester and an L-amino acid. A DNA consisting of the base sequence consisting of bases numbers 57 to 1295 described in SEQ ID NO: 4 of the Sequence Listing was isolated from *Corynebacterium glutamicum* strain ATCC 13286. In addition, a DNA consisting of the base sequence consisting of bases numbers 486 to 1496 described in SEQ ID NO: 14 of the Sequence Listing was isolated from *Pseudomonas putida* strain ATCC 12633. Moreover, a DNA consisting of the base sequence consisting of bases numbers 311 to 1279 described in SEQ ID NO: 16 of the Sequence Listing was isolated from *Pseudomonas putida* strain FERM BP-8123. Note that in the present specification, "base sequence described in SEQ ID NO: 4", "base sequence described in SEQ ID NO: 14", and "base sequence described in SEQ ID NO: 16" refer to the CDS portions unless specifically indicated otherwise.

An example of isolating DNA is shown. First, the amino acid sequence of a purified peptide-forming enzyme is first determined. The amino acid sequence can be determined using Edman's method (see Edman, P., Acta Chem. Scand., 4, 227 (1950)). In addition, the amino acid sequence can also be determined using a sequencer manufactured by Applied Biosystems. The amino acid sequence is determined for the N-terminal or about 10 to 30 residues of the peptide obtained by treatment with lysyl endopeptidase and so forth for the purified peptide-forming enzyme, and the base sequence of DNA that encodes it can be deduced based on the determined amino acid sequence. Universal codons are employed for deducing the base sequence of the DNA.

Then, a DNA molecule of about 30 base pairs is synthesized based on the deduced base sequence. A method for synthesizing this DNA molecule is disclosed in Tetrahedron Letters, 22, 1859 (1981). In addition, the DNA molecule can also be synthesized using a sequencer manufactured by Applied Biosystems. A DNA that encodes peptide-forming enzyme can then be amplified from a chromosomal DNA by the PCR method using the DNA molecule as a primer. However, since the DNA that has been amplified using the PCR method does not contain the full-length DNA that encodes peptide-forming enzyme, the full-length DNA that encodes peptide-forming enzyme is isolated from a chromosomal gene library of various microbial cells such as *Corynebacterium glutamicum, Pseudomonas putida* or *Bacillus subtilis* using the DNA amplified by the PCR method as a probe.

Alternatively, in the case where a portion of the base sequence of the gene is known, the full-length DNA that encodes a peptide-forming enzyme can be isolated from a chromosomal gene library using the DNA having the known sequence as a probe.

Moreover, in the case where the base sequence of the gene has homology with a known sequence, the full-length DNA that encodes a peptide-forming enzyme can be isolated from a chromosomal gene library using a DNA having the known sequence as a probe.

The procedure for the PCR method is described in, for example, White, T. J. et al., Trends Genet., 5, 185 (1989). A method for preparing a chromosomal DNA, as well as a method for isolating a target DNA molecule from a gene library using a DNA molecule as a probe, are described in Molecular Cloning, 2nd edition, Cold Spring Harbor Press (1989).

A method for determining the base sequence of isolated DNA that encodes a peptide-forming enzyme is described in A Practical Guide to Molecular Cloning, John Wiley & Sons, Inc. (1985). In addition, the base sequence can also be determined using a DNA sequencer (Applied Biosystems). DNAs that encode peptide-forming enzymes isolated from *Corynebacterium glutamicum* strain ATCC 13286, *Pseudomonas putida* strain ATCC 12633, and *Pseudomonas putida* strain FERM BP-8123 in this manner are shown in SEQ ID NOs: 4, 14, and 16, respectively.

DNAs that can be used in the present invention are not only the DNAs specified by SEQ ID NOs: 4, 14, and 16. For example, in explaining the DNA of SEQ ID NO: 4 isolated from *Corynebacterium glutamicum* strain ATCC 13286 below, even a DNA that has been artificially mutated to a DNA that encodes a peptide-forming enzyme isolated from the chromosomal DNA of *Corynebacterium glutamicum* strain ATCC 13286 is also a DNA of the present invention so far as it encodes a peptide-forming enzyme. A frequently used method for artificial mutating a DNA is the site-directed mutagenesis method described in Methods in Enzymol., 154 (1987).

In addition, a DNA having a base sequence which hybridizes under stringent conditions with a polynucleotide having a base sequence complementary to a base sequence described in SEQ ID NO: 4 of the Sequence Listing, and encodes a protein having peptide-forming enzyme activity, can also be used as a DNA in the present invention.

Moreover, a DNA substantially identical to the DNA of the present invention can also be obtained by isolating a DNA that hybridizes under stringent conditions with a probe prepared based on a DNA consisting of the CDS described in SEQ ID NO: 4 of the Sequence Listing, and encodes protein having peptide-forming enzyme activity. A probe can be prepared according to established methods based on, for example, the base sequence described in SEQ ID NO: 4 of the Sequence Listing. In addition, a method in which a target DNA is isolated by using a probe and picking up a DNA that hybridizes with it may also be carried out in accordance with established methods. For example, a DNA probe can be prepared by amplifying a base sequence cloned in a plasmid or phage vector and extracting the base sequence desired to be used as a probe by cleaving with a restriction enzyme. The location where the sequence is cleaved can be adjusted corresponding to the target DNA.

The "stringent conditions" mentioned herein refer to conditions under which a so-called specific hybrid is formed while non-specific hybrids are not formed. Although it is difficult to clearly quantify these conditions, examples of such conditions include conditions under which a DNA having a high degree of homology, such as a DNA having a homology of 50% or more, preferably 80% or more, and more preferably 90% or more, hybridizes while a DNA having a low degree of homology does not hybridize, or conditions under which a DNA hybridizes at 60° C. and at a salt concentration equivalent to 1×SSC and 0.1% SDS, which are the conditions for washing of ordinary Southern hybridization, preferably at 60° C. and at a salt concentration equivalent to 0.1×SCC and 0.1% SDS, and more preferably at 65° C. and at a salt concentration equivalent to 0.1×SSC, and 0.1% SDS. The activity of a peptide-forming enzyme is as previously explained. However, in the case of a base sequence that hybridizes under stringent conditions with a base sequence complementary to the base sequence described in SEQ ID NON: 4 of the Sequence Listing, it preferably retains 10% or more, and preferably 50% or more, of the enzyme activity of a protein having the amino acid sequence described in SEQ ID NO: 4 of the Sequence Listing under conditions of 50° C. and pH 8.

Moreover, a protein substantially identical to the peptide-forming enzyme encoded by a DNA described in SEQ ID NO: 4 of the Sequence Listing can also be used in the present invention. Thus, a DNA that encodes "a protein having an amino acid sequence including substitution, deletion, insertion, addition or inversion of one or a plurality of amino acids in the amino acid sequence described in SEQ ID NO: 5 of the Sequence Listing, and having peptide-forming enzyme activity to catalyze a reaction that produces a dipeptide from an L-amino acid ester and an L-amino acid" can also be used in the present invention. The term "a plurality of" refers to that over a range that does not significantly impair the three-dimensional structure of the protein of the amino acid residues or the activity of a peptide-forming enzyme, and more specifically is a value of 2 to 50, preferably a value of 2 to 30, and more preferably a value of 2 to 10. In addition, the activity of a peptide-forming enzyme is as previously explained. However, in the case of an amino acid sequence including substitution, deletion, insertion, addition or inversion of one or a plurality of amino acid residues in the amino acid sequence described in SEQ ID NO: 5 of the Sequence Listing, it preferably retains 10% or more, and preferably 50% or more, of the enzyme activity of a protein having the amino acid sequence described in SEQ ID NO: 5 of the Sequence Listing under conditions of 50° C. and pH 8.

As has been described above, in addition to a DNA isolated from *Corynebacterium glutamicum* strain ATCC 13286, a DNA isolated from *Pseudomonas putida* strain ATCC 12633 and a DNA isolated from *Pseudomonas putida* strain FERM BP-8123, DNAs substantially identical to these DNAs are also provided as DNAs of the present invention. Namely, examples of DNAs provided by the present invention are as follows:

(i) A DNA consisting of a CDS described in SEQ ID NO: 4, 14, or 16 of the Sequence. Listing;

(ii) A DNA that hybridizes under stringent conditions with a polynucleotide consisting of a base sequence complementary to the CDS described in SEQ ID NO: 4, 14, or 16 of the Sequence Listing, and encodes a protein having peptide-forming enzyme activity to catalyze a reaction that produces a dipeptide from an L-amino acid ester and an L-amino acid;

(iii) A DNA that encodes protein having the amino acid sequence described in SEQ ID NO: 5, 15, or 17 of the Sequence Listing; and, (iv) A DNA that encodes a protein having an amino acid sequence that includes substitution, deletion, insertion, addition or inversion of one or a plurality of amino acids in the amino acid sequence described in SEQ ID NO: 5, 15 or 17 of the Sequence Listing, and has peptide-forming enzyme activity to catalyze a reaction that produces a dipeptide from an L-amino acid ester and an L-amino acid.

[II-2] Production of Transformant

Next, production of a transformant that expresses a protein having peptide-forming enzyme activity will be described. Numerous examples are known for producing enzymes, physiologically active substances and other useful proteins by using a recombinant DNA technology, and the use of recombinant DNA technology allows useful proteins present only in trace amounts in nature to be produced in large volumes.

Preferable examples of transformants that can be used in the method of the present invention include the transformants capable of expressing a protein of (AA), (BB), (CC) below, or the like:

(AA) a protein having an amino acid sequence described in SEQ ID NO: 5, 15, or 17 of the Sequence Listing;

(BB) a protein having an amino acid sequence that includes substitution, deletion, insertion, addition or inversion of one or a plurality of amino acids in the amino acid sequence described in SEQ ID NO: 5, 15, or 17 of the Sequence Listing, and has peptide-forming enzyme activity to catalyze a reaction that produces a dipeptide from an L-amino acid ester and an L-amino acid; or, (CC) a protein encoded by a DNA that hybridizes under stringent conditions with a polynucleotide consisting of a base sequence complementary to the base sequence of SEQ ID NO: 4, 16, or 18 of the Sequence Listing or a probe prepared based on the base sequence of SEQ ID NO: 4, 16, or 18, and encodes protein having peptide-forming enzyme activity to catalyze a reaction that produces a dipeptide from an L-amino acid ester and an L-amino acid.

To produce transformants that expresses a protein having peptide-producing activity of the aforementioned (AA) to (CC), a DNA of (i), (ii), (iii), or (iv) indicated in the aforementioned section [II-1] may be inserted into host cells. Namely, a DNA of (i), (ii), (iii), or (iv) is incorporated into a recombinant DNA, and more specifically an expression vector, capable of being expressed in the host cells, followed by introduction of this expression vector into host cells.

In addition, variants like those indicated in the aforementioned (BB) are obtained by modifying the base sequence so that an amino acid at a specific site of the enzyme gene is substituted, deleted, inserted or added by, for example, a site-directed mutagenesis method. In addition, the modified DNA mentioned above can also be acquired by a conventional mutagenesis treatment. Examples of mutagenesis treatment include a method in which a DNA encoding the present enzyme is treated in vitro with hydroxylamine and so forth, and a method in which *Escherichia coli* possessing a DNA encoding the present enzyme is treated with ultraviolet radiation or N-methyl-N'-nitro-N-nitrosoguanidine (NTG), nitrous acid or other mutagen ordinarily used in artificial mutagenesis.

In the case of mass production of a protein using a recombinant DNA technology, a mode of conjugating the protein in a transformant that produces the protein to form an inclusion body of protein is also a preferable mode for carrying out the present invention. Advantages of this expression and production method include protection of the target protein from digestion by proteases present in microbial cells, and simple purification of the target protein by crushing the microbial cells, followed by centrifugation.

The inclusion bodies of protein obtained in this manner are solubilized with a protein denaturant and then converted to a properly folded, physiologically active protein after going through an activity regeneration procedure consisting primarily of removing the denaturant. There are numerous examples of this, including regeneration of the activity of human interleukin-2 (Japanese Patent Application Laid-Open Publication No. S61-257931) and so forth.

To obtain active protein from inclusion bodies of protein, a series of operations including solubilization and activity regeneration are required, and the procedure is more complex than in the case of producing active protein directly. However, in the case of producing in microbial cells a large amount of protein that has a detrimental effect on microbial growth, that effect can be suppressed by accumulating the protein in the form of protein inclusion bodies of protein that are inactive in the microbial cells.

Examples of methods for producing a large volume of a target protein in the form of inclusion bodies include a method in which a target protein is expressed alone under the control of a powerful promoter, and a method in which a target protein is expressed in the form of a fused protein with a protein that is known to be expressed in a large volume.

Moreover, it is also effective to arrange the recognition sequence of a restricting protease at a suitable location in order to cleave the target protein after the expression in the form of a fused protein.

In the case of mass production of a protein using a recombinant DNA technology, examples of host cells that can be used include bacterial cells, *Actinomyces* cells, yeast cells, mold cells, plant cells and animal cells, intestinal bacteria such as *Escherichia coli* are commonly used, with *Escherichia coli* being used preferably. This is because there are numerous findings available regarding techniques for mass production of protein using *Escherichia coli*. Hereinafter, one mode of the method for producing a peptide-forming enzyme using transformed *Escherichia coli* will be described.

Promoters normally used in heterogeneous protein production in *Escherichia coli* can be used as a promoter for expressing DNA encoding peptide-forming enzyme, examples of which include powerful promoters such as T7 promoter, lac promoter, trp promoter, trc promoter, tac promoter, lambda phage $P_R$ promoter, and $P_L$ promoter.

In order to produce a peptide-forming enzyme in the form of an inclusion body of fused protein, a gene that encodes another protein, and preferably a hydrophilic peptide, is coupled to the upstream or downstream of the peptide-forming enzyme gene to obtain a fused protein gene. The gene that encodes another protein in this manner may be any one that increases the amount of fused protein accumulated, and enhances the solubility of the fused protein after the denaturing and regenerating steps. Candidates therefor include, for example, T7 gene 10, β-galactosidase gene, dehydrofolate reductase gene, interferon γ gene, interleukin-2 gene and prochymosin gene.

When coupling these genes to a gene encoding a peptide-forming enzyme, the codon reading frames are made consistent with each other. They may be coupled at a suitable restriction enzyme site or a synthetic DNA of a suitable sequence may be used.

In addition, to increase the production amount, it is preferable in some cases to couple a transcription terminating sequence in the form of a terminator downstream of the fused protein gene. Examples of this terminator include a T7 terminator, an fd phage terminator, a T4 terminator, a tetracycline resistance gene terminator and *Escherichia coli* trpA gene terminator.

So-called multi-copy vectors are preferable as the vector for introducing into *Escherichia coli* a gene that encodes a peptide-forming enzyme or a fused protein consisting of a peptide-forming enzyme and another protein, examples of which include plasmids having a replicator derived from ColE1 such as pUC plasmid, pBR322 plasmid or derivatives thereof. The "derivative" as used herein refers to those plasmids that are subjected to modification of the plasmid by base substitution, deletion, insertion, addition or inversion. Note that the modification referred to here includes modification resulting from mutagenesis treatment by a mutagen or UV irradiation, or spontaneous mutation. More specifically, examples of vectors that can be used include pUC19, pUC18, pBR322, pHSG299, pHSG298, pHSG399, pHSG398, RSF1010, pMW119, pMW118, pMW219 and pMW218. Besides, vectors of phage DNA and transposon DNA can also be used.

In addition, the vector preferably has a marker such as an ampicillin resistance gene in order to screen out the transformant. Expression vectors having powerful promoters are commercially available for use as such plasmids (such as pUC vector (manufactured by Takara Shuzo), pPROK vector (manufactured by Clontech) and pKK233-2 (manufactured by Clontech) and others).

A recombinant DNA is obtained by coupling a DNA fragment, in which a promoter, gene encoding peptide-forming enzyme or fused protein consisting of peptide-forming enzyme and another protein, and depending on the case, a terminator are coupled in that order, with a vector DNA.

When *Escherichia coli* is transformed using the recombinant DNA and the resulting *Escherichia coli* is cultured, a peptide-forming enzyme or a fused protein consisting of the peptide-forming enzyme and another protein is expressed and produced. Although a strain of the transformed host can be used that is normally used in the expression of a heterogeneous gene, *Escherichia coli* strain JM109 is preferable. Methods for carrying out transformation and methods for screening out transformants are described in Molecular Cloning, 2nd Edition, Cold Spring Harbor Press (1989) and other publications.

In the case of expressing the protein in the form of a fused protein, the fused protein may be prepared such that a peptide-forming enzyme can be cleaved out using a restriction protease that uses a sequence not present in the peptide-forming enzyme, such as blood coagulation factor Xa or kallikrein, as the recognition sequence.

A medium normally used for culturing *Escherichia coli*, such as an M9-casamino acid medium or an LB medium, may be used as the production medium. In addition, culturing conditions and production induction conditions are suitably selected according to the marker of the vector used, promoter, type of host microbe and so forth.

The following method can be used to recover a peptide-forming enzyme or a fused protein consisting of the peptide-forming enzyme and another protein. If the peptide-forming enzyme or its fused protein has been solubilized in the microbial cells, after recovering the microbial cells, the microbial cells are crushed or lysed so that they can be used as a crude enzyme liquid. Moreover, the peptide-forming enzyme or its fused protein can be purified prior to use by ordinary techniques such as precipitation, filtration or column chromatography as necessary. In this case, a purification method can also be used that uses antibody to the peptide-forming enzyme or its fused protein.

In the case where inclusion bodies of protein are formed, the inclusion bodies are solubilized with a denaturant. Although they may be solubilized with the microbial cell protein, in consideration of the following purification procedure, the inclusion bodies are preferably taken out and then solubilized. Conventionally known methods may be used to recover the inclusion bodies from the microbial cells. For example, inclusion bodies can be recovered by crushing the microbial cells, followed by centrifugation. Examples of denaturants capable of solubilizing inclusion bodies include guanidine hydrochloride (for example, 6 M, pH 5 to 8) and urea (for example, 8 M).

Protein having activity is regenerated by removing these denaturants by dialysis. Tris-HCl buffer solution or phosphate buffer solution and so forth should be used as the dialysis solution used in dialysis, and the concentration may be, for example, 20 mM to 0.5 M, while the pH may be, for example, 5 to 8.

The protein concentration during the regeneration step is preferably held to about 500 μg/ml or less. The dialysis temperature is preferably 5° C. or lower to inhibit the occurrence of self-crosslinking by the regenerated peptide-forming enzyme. In addition, dilution or ultrafiltration may be used in addition to dialysis to remove the denaturants, and the enzyme activity can be expected to be regenerated no matter which a denaturant is used.

In the case of using the DNA indicated in SEQ ID NO: 4 of the Sequence Listing for the DNA that encodes a peptide-forming enzyme, the peptide-forming enzyme is produced that has the amino acid sequence described in SEQ ID NO: 5. In addition, in the case of using a DNA indicated in SEQ ID NO: 14 of the Sequence Listing as the DNA that encodes a peptide-forming enzyme, peptide-forming enzyme is produced that has the amino acid sequence described in SEQ ID NO: 15. In addition, in the case of using a DNA indicated in SEQ ID NO: 16 of the Sequence Listing as the DNA that encodes a peptide-forming enzyme, peptide-forming enzyme is produced that has the amino acid sequence described in SEQ ID NO: 17.

Note that genetic engineering techniques can be carried out in compliance with the techniques described in the literature such as Molecular Cloning, 2nd edition, Cold Spring Harbor Press (1989).

[III] Properties of Peptide-Forming Enzyme

Next, the properties of a peptide-forming enzyme purified from *Corynebacterium glutamicum* strain ATCC 13286 as an example of the aforementioned microbes.

Taking an example of using an L-alanine ester and L-glutamine as raw materials (substrates), this peptide-forming enzyme has activity to produce L-alanyl-L-glutamine using an L-alanine ester and L-glutamine as substrates. In addition, taking an example of using L-alanine ester and L-asparagine as raw materials, this peptide-forming enzyme has activity to produce L-alanyl-L-asparagine using an L-alanine ester and L-asparagine as substrates.

With respect to the enzyme action, taking an example of using an L-alanine ester and L-asparagine or L-glutamine as raw materials, this peptide-forming enzyme produces one molecule of L-alanyl-L-glutamine and one molecule of alcohol from one molecule of L-alanine ester and one molecule of L-glutamine, and produces one molecule of L-alanyl-L-asparagine and one molecule of alcohol from one molecule of L-alanine ester and one molecule of asparagine.

The optimum pH is in the vicinity of 6.0 to 10.0, and the optimum temperature is in the vicinity of 30° C. to 50° C. The molecular weight of the subunit is calculated to be 42,000 to 46,000 as determined by SDS-polyacrylamide gel electrophoresis.

[IV] Dipeptide Production Method

The dipeptide production method of the present invention produces a dipeptide from an L-amino acid ester and an L-amino acid using an enzyme or enzyme-containing substance having the ability to synthesize a dipeptide, and more specifically, produces a dipeptide from an L-amino acid ester and an L-amino acid using a peptide-forming enzyme derived from a culture of microbes, microbial cells isolated from the culture or treated microbial cell product of the microbe having the ability to produce a dipeptide from an L-amino acid ester and an L-amino acid. Note that a protein having proline iminopeptidase activity derived from the aforementioned microbes or those listed in the following Table 1 can also be used so far as they have activity to produce a dipeptide from an L-amino acid ester and an L-amino acid.

The peptide-forming enzyme produced by the aforementioned microbes has activity to produce a dipeptide by using an L-amino acid ester and an L-amino acid as substrates.

As the method by which the peptide-forming enzyme produced by the aforementioned microbes is allowed to act on the L-amino acid ester and L-amino acid, the substrates may be added directly to the culture liquid while culturing the aforementioned microbes, or microbial cells may be separated from the microbial culture by centrifugation and so forth, followed by either re-suspending in buffer either directly or after washing, and then adding an L-amino acid ester and an L-amino acid and allowing them to react. Alternatively, microbial cells can be used that have been immobilized by a known method using polyacrylamide gel, carrageenan or alginic acid gel.

In addition, crushed microbial cells, acetone-treated microbial cells or freeze-dried microbial cells may be used as the treated microbial cell product. Methods such as ultrasonic crushing, French press crushing or glass bead crushing can be used for crushing microbial cells, while methods using egg white lysozyme, peptidase treatment or a suitable combination thereof are used in the case of lysing microbial cells.

Moreover, a peptide-forming enzyme may be recovered from the treated microbial cell product and used as a crude enzyme liquid, or the enzyme may be purified before use as necessary. Ordinary enzyme purification methods can be used for purifying the enzyme obtained from a culture. More specifically, microbial cells are collected by centrifugation and so forth, the cells are then crushed by mechanical methods such as ultrasonic treatment, glass beads or a dynomill, and solid materials such as cell fragments are removed by centrifugation to obtain crude enzyme followed by purification of the aforementioned peptide-forming enzyme by performing ultracentrifugation fractionation, salting out, organic solvent precipitation, ion exchange chromatography, adsorption chromatography, gel filtration chromatography, hydrophobic chromatography and so forth.

Note that the "peptide-forming enzyme derived from a microbe" includes not only an enzyme obtained from the treated microbial cell product by going through the aforementioned purification step, but also enzyme produced by so-called genetic engineering techniques in which the gene of the enzyme is expressed in a heterogeneous or homogeneous host.

Namely, in the case of a fraction having activity to produce a dipeptide from an L-amino acid ester and an L-amino acid, the whole enzyme and enzyme-containing substance can be used. Here, an "enzyme-containing substance" refers to that which contains the enzyme, and includes specific forms such as a culture of microbes that produce the enzyme, microbial cells separated from the culture and treated microbial cell products of the microbes. A culture of microbes refers to that which is obtained by culturing microbes, and more specifically, refers to a mixture of microbial cells, the medium used to culture the microbes and substances produced by the cultured microbes. In addition, the microbial cells may be washed and used as washed microbial cells. The treated microbial cell product includes cells that have been crushed, lysed or freeze-dried, and further include a crude enzyme recovered by treating the cells and so forth as well as purified enzyme resulting from its purification. Partially purified enzymes and so forth obtained by various purification methods may also be used as purified enzymes, or immobilized enzyme may be used that have been immobilized by covalent bonding, adsorption or entrapment methods. In addition, since some microbes are partially lysed during culturing depending on the microbes used, the culture supernatant may also be used as the enzyme-containing substance in such cases.

Note that in the case of using a culture, cultured microbial cells, washed microbial cells or processed microbial cells in which the cells have been crushed or lysed, there are many cases in which an enzyme is present that decomposes the peptide produced without being involved in peptide production, and in such cases, there are cases in which it is preferable to add a metallic enzyme inhibitor such as a metalloprotease inhibitor like, for example, ethylenediaminetetraacetic acid (EDTA). The amount added is in the range of 0.1 mM to 100 mM, and preferably 1 mM to 50 mM.

The amount of enzyme or enzyme-containing substance used may be enough if it is an amount in which the target effect is demonstrated (effective amount). This effective amount can be easily determined through simple, preliminary experimentation by a person with ordinary skill in the art; for example, in the case of using washed cells, the amount used is 1 to 500 g/l of reaction liquid.

Any L-amino acid ester can be used as the L-amino acid ester so far as it is an L-amino acid ester capable of producing dipeptide with L-amino acid at the substrate specificity of the peptide-forming enzyme, and examples of such include methyl esters, ethyl esters, n-propyl esters, iso-propyl esters, n-butyl esters, iso-butyl esters and tert-butyl esters of L-amino acids. In addition, not only L-amino acid esters corresponding to naturally-occurring amino acids, but also L-amino acid esters corresponding to non-naturally-occurring amino acids or their derivatives can also be used. Examples of L-amino acid esters that can be used preferably in the present invention include L-alanine ester, glycine ester, L-valine ester, L-isoleucine ester, L-methionine ester, L-phenylalanine ester, L-serine ester, L-threonine ester, L-glutamine ester, L-tyrosine ester, L-arginine ester, L-aspartic acid-α-ester, L-aspartic acid-β-ester, L-leucine ester, L-asparagine ester, L-lysine ester, L-aspartic acid-α,β-dimethyl ester and L-glutamine-γ-ester.

There is no particular restriction on the L-amino acid and any L-amino acid can be used so far as it produces a dipeptide with an L-amino acid ester in the substrate specificity of the peptide-forming enzyme. Examples of L-amino acids that can be used preferably in the present invention include L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine, and L-glutamate, with L-glutamine and L-asparagine being particularly preferable.

Each concentration of the L-amino acid ester and L-amino acid used as starting materials is 1 mM to 10 M, and preferably 0.05 M to 2 M. However, there are cases in which it is preferable to add an equimolar amount or more of L-amino acid with respect to the amount of L-amino acid ester. In addition, in the case where a high concentration of substrate inhibits the reaction, it can be adjusted to a concentration that does not cause inhibition and then successively added during the reaction.

The reaction temperature is 3 to 70° C., and preferably 5 to 50° C., while the reaction pH is 2 to 12, and preferably 3 to 11. By carrying out the reaction in this manner for about 2 to 48 hours, a dipeptide is produced and accumulates in the reaction mixture. The resulting dipeptide can then be recovered by established methods and purified as necessary.

EXAMPLES

Hereinafter, the present invention will be described in detail by referring to the examples described below. However, the present invention is not limited to these examples. Note that in the examples, quantitative determination of L-alanine, L-alanyl-L-glutamine or L-alanyl-L-asparagine was carried out by a method using high performance liquid chromatography (column: Inertsil ODS-2 (GL Science), eluate: aqueous phosphate solution (pH 2.2, 5.0 mM sodium 1-octane sulfonate/methanol=100/15), flow rate: 1.0 mL/min, detection: 210 nm).

Example 1

Effect of Addition of EDTA on Production of L-Alanyl-L-Glutamine 50 mL of a medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract and 10 g of peptone in 1 L was transferred to a 500 mL Sakaguchi flask and sterilized for 15 minutes at 115° C. One loopful of *Pseudomonas putida* strain FERM BP-8101, which had been cultured for 24 hours at 30° C. on an slant agar medium containing the same composition (agar: 20 g/L, pH 7.0), was inoculated into the aforementioned medium and cultured by shake culturing for 17 hours at 30° C. and 120 strokes/minute. Following culturing, the microbial cells were separated by centrifugation and suspended with 100 mM borate buffer (pH 9.0) to a wet cell density of 100 g/L. 1 mL each of the cell suspension was respectively added to 1 mL of 100 mM borate buffer (pH 9.0) containing 200 mM L-alanine ethyl ester hydrochloride and 400 mM L-glutamine either in the absence of EDTA or additionally containing 20 mM EDTA (substrate solution) to bring to a final volume of 2 mL followed by allowing to react for 1 hour at 30° C. As a result, L-alanyl-L-glutamine was produced at 4.9 mM in the section added with no EDTA and at 10.1 mM in the section added with EDTA.

Note that in this reaction system, under conditions in which 1 mL of 100 mM borate buffer (pH 9.0) instead of cell suspension was added to 1 mL of substrate solution (cell-free lot) and under conditions in which 1 mL of 100 mM of borate buffer either free of EDTA or containing 20 mM EDTA but not containing L-alanine ethyl ester hydrochloride and glutamine was added to the cell suspension (substrate-free lot), production of L-alanyl-L-glutamine was not observed in either case.

Example 2

Use of Amino Acid Ester as Substrate 1 mL of cell suspension wet cells (100 g/L) of *Pseudomonas putida* strain FERM BP-8101 prepared in the same manner as Example 1 was respectively added to 1 mL of 100 mM borate buffer (pH 9.0) containing 20 mM EDTA and the following L-alanine ester hydrochlorides at 200 mM and L-glutamine at 400 mM to bring to a final volume of 2 mL, followed by allowing to react for 1 hour at 30° C. As a result, 14.9 mM L-alanyl-L-glutamine was produced in the case of using L-alanine methyl ester hydrochloride and L-glutamine as substrates, 11.4 mM L-alanyl-L-glutamine was produced in the case of using L-alanine ethyl ester hydrochloride and L-glutamine as substrates, and 0.5 mM L-alanyl-L-glutamine was produced in the case of using L-alanine-tert-butyl ester hydrochloride and L-glutamine as substrates.

Example 3

Use of L-Amino Acid as Substrate 1 mL of a cell suspension wet cells (100 g/L) of *Pseudomonas putida* strain FERM BP-8101 prepared in the same manner as Example 1 was respectively added to 1 mL of 100 mM borate buffer (pH 9.0) containing 20 mM EDTA and the following L-alanine ester hydrochlorides at 200 mM and L-glutamine or L-asparagine at 400 mM to bring to a final volume of 2 mL, followed by allowing to react for 1 hour at 30° C. As a result, 12.7 mM L-alanyl-L-glutamine was produced in the case of using L-alanine methyl ester hydrochloride and L-glutamine as substrates, and 4.8 mM L-alanyl-L-asparagine was produced in the case of using L-alanine methyl ester hydrochloride and L-asparagine as substrates.

Example 4

Microbes Producing L-Alanyl-L-Glutamine 50 mL of a medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract and 10 of peptone in 1 L was transferred to a 500 mL Sakaguchi flask and sterilized for 15 minutes at 115° C. One loopful of each of the bacteria shown in Table 1, which had been cultured for 24 hours at 30° C. on an slant agar medium (agar: 2 g/L, pH 7.0) containing 5 g of glucose, 10 g of yeast extract, 10 g of peptone and 5 g of NaCl, was inoculated into the aforementioned medium and cultured by shake culturing for 17 hours at 30° C. and 120 strokes/minute. After the culturing, the microbial cells were separated by centrifugation and suspended with 0.1 M borate buffer (pH 9.0) containing 10 mM EDTA to 100 g/L as wet microbial cells. 0.1 mL of 100 mM borate buffer (pH 9.0) containing 10 mM EDTA, 200 mM L-alanine methyl ester hydrochloride and 400 mM L-glutamine was respectively added to 0.1 mL of these microbial cell suspensions to bring to a final volume of 0.2 mL followed by allowing to react for 2 hours at 25° C. The amounts (mM) of L-alanyl-L-glutamine (Ala-Gln) produced at this time are shown in Table 1.

TABLE 1

| Microbe | Ala-Gln (mM) |
| --- | --- |
| *Bacillus subtilis* ATCC 6633 | 1.1 |
| *Corynebacterium glutamicum* ATCC 13286 | 7.2 |
| *Pseudomonas putida* FERM BP-8101 | 14.8 |

Example 5

Effect of Temperature on Production of L-Alanyl-L-Glutamine 1 mL of the suspension of *Pseudomonas putida* strain FERM BP-8101 cells (100 g/L) prepared in accordance with the microbe culturing method of Example 4 was respectively added to 1 mL of 100 mM borate buffer (pH 9.0) containing 10 mM EDTA, 200 mM L-alanine methyl ester hydrochloride and 400 mM L-glutamine to bring to a final volume of 2 mL, followed by allowing to react for 1 hour at temperatures of 20° C., 300° C. and 40° C., respectively. Those results are shown in Table 2. Production of L-alanyl-L-glutamine (Ala-Gln) demonstrated the highest value at a temperature of 40° C. in the case of *Pseudomonas putida* strain FERM BP-8101.

TABLE 2

| Microbe | Ala-Gln Produced (mM) | | |
| --- | --- | --- | --- |
| | 20° C. | 30° C. | 40° C. |
| *Pseudomonas putida* FERM BP-8101 | 8.2 | 16.9 | 20.8 |

Example 6

Purification of Peptide-Forming Enzyme from *Corynebacterium glutamicum* strain ATCC 13286 and Production of L-Alanyl-L-Glutamine by the Purified Enzyme 500 mL of a medium containing 5 g of glycerol, 5 g of yeast extract, 5 g of peptone, 5 g of sodium chloride and 5 g of L-alanine amide hydrochloride in 1 L was transferred to a 5 L Sakaguchi flask and sterilized for 20 minutes at 120° C. Culture liquid of *Corynebacterium glutamicum* strain ATCC 13286 cultured for 20 hours in medium of the same composition as above was inoculated into the medium to be 5% (v/v), and cultured for 20 hours at 30° C. and 120 strokes/minute. Microbial cells were collected from 8 L of this culture liquid by centrifugation. The subsequent procedure was carried out either on ice or at 4° C. After washing the microbial cells with 50 mM potassium phosphate buffer (pH 7.0), the cells were subjected to crushing treatment for about 10 minutes using glass beads having a diameter of 0.1 millimeter. The glass beads and crushed cell liquid were then separated, and the crushed cell fragments were removed by centrifugation for 30 minutes at 20,000×gravity (g) to obtain a cell-free extract. Moreover, the insoluble fraction was removed by ultracentrifugation for 60 minutes at 200,000×g to obtain a soluble fraction in the form of the supernatant. Ammonium sulfate was then added to the resulting soluble fraction to 60% saturation followed by recovery of the precipitate by centrifuging for 30 minutes at 20,000×g. The resulting precipitate was dissolved in a small amount of 50 mM potassium phosphate buffer (pH 7.0) and then dialyzed against 50 mM potassium phosphate buffer (pH 7.0). This enzyme liquid was then applied to a Q-Sepharose HP column pre-equilibrated with 50 mM potassium phosphate buffer (pH 7.0), and the enzyme was eluted over a linear concentration gradient of 50 mM potassium phosphate buffer (pH 7.0) containing 0 to 1.0 M sodium chloride. The active fraction was collected and applied to a Superdex 200 pg column pre-equilibrated with 50 mM potassium phosphate buffer (pH 7.0), and the enzyme was then eluted with the same buffer. The active fraction was collected and dialyzed against 20 mM potassium phosphate buffer (pH 7.0) containing 0.5 M ammonium sulfate, and then applied to a Phenyl-Sepharose HP column pre-equilibrated with 20 mM potassium phosphate buffer (pH 7.0) containing 0.5 M ammonium sulfate. The enzyme was then eluted over a linear concentration gradient of 20 mM potassium phosphate buffer (pH 7.0) containing 0.5 to 0 M ammonium sulfate. The active fraction was collected and dialyzed against 50 mM potassium phosphate buffer (pH 7.0), and this was then applied to a MonoQ column pre-equilibrated with 50 mM potassium phosphate buffer (pH 7.0), after which enzyme was eluted over a linear concentration gradient of 50 mM potassium phosphate buffer (pH 7.0) containing 0 to 1.0 M sodium chloride. The purified peptide-forming enzyme was uniformly purified on the basis of electrophoresis in this manner.

The specific activity of the purified enzyme was 9.841 U/mg, and the specific activity of the purified peptide-forming enzyme was increased about 246-fold as a result of going through these purification steps. In addition, as a result of applying the molecular weight of the purified enzyme standard to SDS polyacrylamide electrophoresis, a uniform band was detected at the position calculated to represent a molecular weight of 42,000 to 46,000. Measurement of enzyme titer was carried out as described below. 200 μM of Tris-HCl buffer (pH 9.0), 50 μM of L-alanine amide and a suitable amount of enzyme liquid were added and mixed to a final volume 1 mL, and after allowing to react for 60 minutes at 30° C., 4 mL of aqueous phosphoric acid (pH 2.1) was added to stop the reaction. The alanine produced was quantified by high-performance liquid chromatography, and the amount of enzyme that produces 1 μM of L-alanine in 1 minute was defined as 1 unit.

This purified enzyme was then added to borate buffer (pH 9.0) containing EDTA, L-alanine methyl ester hydrochloride and L-glutamine (or L-asparagine), mixed to the total volume of 1 mL (for the final concentrations, the amount of enzyme added was 2 units as alanine amide decomposition activity, EDTA was at 10 mM, L-alanine methyl ester hydrochloride was at 100 mM and L-glutamine (or L-asparagine) was at 200 mM borate buffer at 100 mM), and allowed to react for 4 hours at 30° C. (Note that the number of units of enzyme does not indicate the production activity with respect to producing L-alanyl-L-glutamine from L-alanine methyl ester and L-glutamine, but rather simply indicates L-alanine amide decomposition activity.) The amount of L-alanyl-L-glutamine produced at this time was 50.2 mM, while the amount of L-alanyl-L-asparagine produced was 49.8 mM.

Example 7

Isolation of Peptide-Forming Enzyme Gene from *Corynebacterium glutamicum* Strain ATCC 13286 and Expression in *Escherichia coli*

Hereinafter, the isolation of a peptide-forming enzyme gene from *Corynebacterium glutamicum* strain ATCC 13286 and its expression in *Escherichia coli* (*Escherichia coli*) will be described. *Escherichia coli* JM109 was used as the host and pUC18 was used as the vector for both the isolation and expression of the gene.

1. Production of PCR Primer Based on Determined Amino Acid Sequence

Mixed primers indicated in SEQ ID NO: 2 and SEQ ID NO: 3, respectively, were produced based on the N-terminal amino acid sequence of peptide-forming enzyme derived from the *Corynebacterium glutamicum* strain ATCC 13286 (SEQ ID NO:1) obtained in Example 1.

2. Microbe Acquisition

The microbes were refreshed by culturing *Corynebacterium glutamicum* strain ATCC 13286 for 24 hours at 30° C. on a CM2Gly agar medium (0.5 g/dL glycerol, 1.0 g/dL yeast extract, 1.0 g/dL peptone, 0.5 g/dL NaCl, 2 g/dL agar, pH 7.0). One loopful of cells was then inoculated into a 500 mL Sakaguchi flask containing 50 mL of CM2Gly liquid medium, followed by shake culturing for 16 hours at 30° C. under aerobic conditions.

3. Acquisition of Chromosomal DNA from Microbial Cells 50 mL of culture liquid was centrifuged (12,000 revolutions per minute, 4° C., 15 minutes) to collect the microbial cells. These microbial cells were then suspended in 10 mL of 50 mM Tris-HCl buffer (pH 8.0) containing 20 mM EDTA followed by recovery of the microbial cells by centrifugation. The microbial cells were again suspended in 10 mL of 50 mM Tris-HCl buffer (pH 8.0) containing 20 mM EDTA. Moreover, after adding 0.5 mL of 20 mg/ml lysozyme solution and 1 mL of 10% SDS (sodium dodecyl sulfate) solution to this suspension, the solution was incubated for 20 minutes at 55° C. This incubated solution was then deproteinized by the addition of an equimolar amount of phenol saturated with 10 mM Tris-HCl buffer (pH 8.0) containing 1 mM EDTA. An equimolar amount of 2-propanol was added to the separated aqueous layer to precipitate DNA, followed by recovery of that precipitated DNA. After dissolving the precipitated in DNA in 0.5 mL of 50 mM Tris-HCl buffer (pH 8.0) containing 20 mM EDTA, 5 μL of 10 mg/ml RNase and 5 μL of 10 mg/ml Proteinase K was added and allowed to react for 2 hours at 55° C. After the reaction, this solution was deproteinized by the addition of an equal volume of phenol saturated with 10 mM Tris-HCl buffer (pH 8.0) containing 1 mM EDTA. Moreover, an equal volume of 24:1 chloroform/ isoamyl alcohol was added to the separated aqueous layer followed by stirring and recovery of the aqueous layer. After performing this procedure two times, 3 M sodium acetate solution (pH 5.2) was added to the resulting aqueous layer to bring to a final concentration of 0.4 M followed by the addition of 2 volumes of ethanol. The DNA that formed as a precipitate was recovered, and after washing with 70% ethanol, was dried and dissolved in 1 mL of 10 mM Tris-HCl buffer (pH 8.0) containing 1 mM EDTA.

4. Acquisition of DNA Fragment Containing Partial Peptide-Forming Enzyme Gene by Cassette PCR The TaKaRa LA PCR in vitro Cloning Kit (manufactured by Takara Shuzo) was used for isolation and amplification of DNA molecules containing gene (aah) encoding peptide-forming enzyme using the cassette PCR method. Unless indicated otherwise, the experiment was carried out based on the method described in the manual. In the cassette PCR method, in case of using Primer 1 (1st PCR, SEQ ID NO: 2) and Primer 2 (2nd PCR, SEQ ID NO: 3) as primers, a roughly 0.5 kilobase (kb) band (Fragment 1) was amplified with the Eco RI cassette. As a result of determining the base sequence of this fragment, Fragment 1 was confirmed to be a portion of aah.

5. Cloning of Peptide-Forming Enzyme Gene from Gene Library

Next, in order to acquire the whole length of aah, Southern hybridization was first carried out using Fragment 1 as a probe.

The DNA fragment that serves as the probe was prepared to about 50 ng/μl and the probe was labeled by incubating 16 μL of this DNA solution for 24 hours at 37° C. in accordance with the protocol using DIG High Prime (Boehringer Mannheim).

1 μg of chromosomal DNA was completely digested by use of combinations of various restriction enzymes, and then electophoresed with 0.8% agarose gel. Then, this was blotted onto positively charged Nylon membranes (Boehringer Mannheim, Nylon membranes positively charged). Southern hybridization was then carried out in accordance with the following established method. Hybridization was carried out using DIG Easy Hyb (Boehringer Mannheim), and after hybridization for 30 minutes at 50° C., the probe was added, following by hybridization for 18 hours at 50° C. Detection was carried out using the DIG Nucleotide Detection Kit (Boehringer Mannheim).

As a result, a band was detected at about the 7 kb position in the BglII cleaved product. This 7 kb region fragment was collected and coupled to pUC18 to produce a library (120 strains) with *Escherichia coli* JM109. Colony hybridization was then carried out in accordance with the following established method. The colonies were transferred to Nylon membranes for colony and plaque hybridization (Boehringer Mannheim) followed by alkaline denaturation, neutralization and immobilization treatment. Hybridization was carried out using DIG Easy Hyb. The filter was immersed in buffer and pre-hybridized for 30 minutes at 42° C. Subsequently, the aforementioned labeled probe was added followed by hybridization for 18 hours at 42° C. After washing with SSC buffer, one positive clone was selected using the DIG Nucleotide Detection Kit.

6. Base Sequence of Peptide-Forming Enzyme Gene Derived from *Corynebacterium glutamicum* Strain ATCC 13286

Plasmids retained by the selected transformant were prepared in accordance with the method described in Molecular Cloning, 2nd edition, Cold Spring Harbor Press (1989), and the base sequence in the vicinity that hybridized with the probe was determined. An open reading frame (ORF) was present that encoded a protein containing 30 residues of the N-terminal amino acid sequence of a peptide-forming enzyme, and was confirmed to be gene aah that encodes the peptide-forming enzyme. The base sequence of the full-length peptide-forming enzyme gene is shown in SEQ ID NO: 4 of the Sequence Listing. The resulting ORF exhibited a base sequence homology of 57.6% with known proline iminopeptidase derived from *Propionibacterium* species bacteria. Note that the numerical value of homology is the value obtained by Genetyx (hereinafter the same applies to this Example).

7. Expression of Peptide-Forming Enzyme Gene in *Escherichia coli*

Plasmid PUCAAH coupled to aah downstream of the lac promoter of pUC18 was constructed in order to express aah in *Escherichia coli*. Fragments amplified by PCR using the chromosomal DNA of *Corynebacterium glutamicum* strain ATCC 13286 as template and the oligonucleotides shown in Table 3 as primers were treated with SacI and SmaI, and after ligating with the SacI and SmaI cleaved products of pUC18, were used to transform *Escherichia coli* JM109. Strains having the target plasmid were selected from ampicillin-resistant strains, and the constructed expression plasmid was designated as pUCAAH.

TABLE 3

Primers Used to Construct Peptide-Forming Enzyme Expression Vector

| Primer | Sequence | |
|---|---|---|
| 5' side | GGCGAGCTCGGGCAGTGGTGGGGGTGGTGT SacI | SEQ ID NO: 6 |
| 3' side | CGGGGGCCCTCAGCGTACCTCTCGGCCGTG SmaI | SEQ ID NO: 7 |

The transformant expressing peptide-forming enzyme in *Escherichia coli* having PUCAAH was pre-cultured for 16 hours at 37° C. in an LB medium containing 0.1 mg/ml ampicillin. 1 mL of this pre-culture broth was inoculated into a 500 mL Sakaguchi flask containing 50 mL of LB medium followed by final culturing at 37° C. After 2 hours from the start of the culturing, isopropyl-1-thio-β-D-galactopyranoside (IPTG) was added to a final concentration of 1 mM followed by additionally culturing for 3 hours.

After completion of the culturing, the microbes were collected and washed, suspended in 10 mL of 20 mM phosphate buffer (pH 8.0), and then subjected to ultrasonic crushing for 30 minutes at 180 W. The solution was collected and centrifuged for 10 minutes at 12,000 g×10 minutes, and the resulting supernatant was used as a cell-free extract.

Example 8

Measurement of Activity of Peptide-Forming Enzyme

1. Activity of Enzyme Derived from *Corynebacterium glutamicum* Strain ATCC 13286

After completion of the culturing in the manner described above, a cell-free extract was prepared and the activity of peptide-forming enzyme was measured using this as the enzyme source. Measurement of peptide-forming enzyme activity was carried out by incubating a reaction liquid containing 100 mM L-alanine methyl ester hydrochloride, 150 mM L-glutamine, 100 mM borate buffer (pH 9.0), 10 mM EDTA, and the enzyme solution for 60 minutes at 30° C., followed by stopping the reaction by adding 4 fold volume of phosphoric acid (pH 1.5). The amount of L-alanyl-L-glutamine was determined by HPLC. For the unit of enzyme activity, enzyme activity to produce 1 μmol of L-alanyl-L-glutamine in 1 minute under these conditions was defined as 1 unit (U).

Conditions of HPLC used for analysis are as follows:
Column: Inertsil ODS-2
Mobile phase: (aqueous phosphoric acid solution (pH 2.1)), 2.5 mM
sodium-1-octanesulfonate/methanol=10/1
Column temperature: 40° C.
Flow rate: 1.0 ml/minute
Detection: UV 210 nanometers As a result, 0.54 U/mg of activity that synthesized L-alanyl-L-glutamine from L-alanine methyl ester hydrochloride was detected in the case of introducing pUC18 AAH, thereby confirming that the cloned aah gene was expressed in *Escherichia coli*. Note that no activity was detected in the case of inserting pUC18 only as a control.

2. Expression of His-Tag Peptide-Forming Enzyme Gene in *Escherichia coli*

Plasmid pQEAAH that expresses a peptide-forming enzyme as an His-Tag protein downstream of the lac promoter of pUC18 was constructed to express aah in *Escherichia coli*. Fragments amplified by PCR using the chromosomal DNA of *Corynebacterium glutamicum* strain ATCC 13286 as template and the oligonucleotides shown in Table 4 as primers were treated with SacI and SmaI, and after ligating with the SacI and SmaI cleaved products of pQE-30 (Qiagen), were used to transform *Escherichia coli* JM109. Strains having the target plasmid were selected from ampicillin-resistant strains, and the constructed expression plasmid was designated as pQEAAH.

TABLE 4

Primers Used to Construct His-Tag Peptide-Forming Enzyme Expression Vector

| Primer | Sequence | |
|---|---|---|
| 5' side | GGC <u>GAG CTC</u> ATG ACT AAA ACA<br>SacI<br>CTT GGT TCC | SEQ ID NO: 8 |
| 3' side | CGG <u>GGG CCC</u> TCA GCG TAC CTC<br>SmaI<br>TCG GCC GTG | SEQ ID NO: 7 |

When the activity of the transformant expressing peptide-forming enzyme in *Escherichia coli* having pQEAAH was measured using the same method as in Example 8, it was found to exhibit peptide-forming enzyme activity of 5.28 U/mg.

3. Preparation of His-Tag Purified Enzyme

Microbial cells from 150 mL of culture broth of *Escherichia coli* JM109 possessing pQEAAH were crushed according to the aforementioned method, and His-Tag L-alanine amide hydrolase was purified using the His Trap Kit (manufactured by Amersham Pharmacia Biotech) according to the protocol provided with the kit. 24 mg of protein was acquired that exhibited a single band on SDS-PAGE, and the specific activity of synthesis of L-alanyl-L-glutamine from L-alanine methyl ester hydrochloride was 148.3 U/mg and 50.7% with respect to L-alanine methyl ester hydrochloride.

4. Study of Substrate Specificity Using His-Tag Purified Enzyme

The synthesis of peptides other than the L-alanyl-L-glutamine by the acquired peptide-forming enzyme was studied using His-Tag purified enzyme.

(1) Peptide Synthesis from L-alanine Methyl Ester and Other L-amino Acids

The synthesis reaction was carried out by incubating a reaction liquid containing 100 mM L-alanine methyl ester hydrochloride, 150 mM test amino acid, 100 mM borate buffer (pH 9.0), 10 mM EDTA and enzyme solution (0.05 U/ml) for 3 hours at 25° C., followed by determination of the quantity of the peptides produced by HPLC. As a result, 22.34 mM L-alanyl-L-asparagine was produced in the case of using L-asparagine as the other amino acid, 5.66 mM L-alanyl-glycine was produced in the case of using glycine, 10.63 mM L-alanyl-L-alanine was produced in the case of using L-alanine, 13.73 mM L-alanyl-L-leucine was produced in the case of using L-leucine, 48.80 mM L-alanyl-L-methionine was produced in the case of using L-methionine, 1.02 mM L-alanyl-L-proline was produced in the case of using L-proline, 16.13 mM L-alanyl-L-phenylalanine was produced in the case of using L-phenylalanine, 15.31 mM L-alanyl-L-tryptophan was produced in the case of using L-tryptophan, 26.14 mM L-alanyl-L-serine was produced in the case of using L-serine, 24.23 mM L-alanyl-L-threonine was produced in the case of using L-threonine, 0.96 mM L-alanyl-L-tyrosine was produced in the case of using L-tyrosine, 7.91 mM L-alanyl-L-lysine was produced in the case of using L-lysine, 24.87 mM L-alanyl-L-arginine was produced in the case of using L-arginine, 23.16 mM L-alanyl-L-histidine was produced in the case of using L-histidine, 1.11 mM L-alanyl-L-glutamate was produced in the case of using L-glutamate.

(2) Peptide Synthesis from Other L-Amino Acid Methyl Esters and L-Glutamine

The reactions were carried out using amino acid methyl esters other than L-alanine methyl ester.

The synthesis reaction was carried out by incubating a reaction liquid containing 100 mM test amino acid methyl ester, 150 mM L-glutamine, 100 mM borate buffer (pH 9.0), 10 mM EDTA and enzyme (0.05 U/ml) for 3 hours at 25° C., followed by determination of the quantity of the produced peptides by HPLC. As a result, 52.19 mM glycyl-L-glutamine was produced in the case of using glycine methyl ester as the L-amino acid methyl ester, 5.94 mM L-valyl-L-glutamine was produced in the case of using L-valine methyl ester, 0.59 mM L-isoleucyl-L-glutamine was produced in the case of using L-isoleucyl-L-glutamine, 4.31 mM L-methionyl-L-glutamine was produced in the case of using L-methionine methyl ester, 3.67 mM L-phenylalanyl-L-glutamine was produced in the case of using L-phenylalanine methyl ester, 40.44 mM L-seryl-L-glutamine was produced in the case of using L-serine methyl ester, 3.85 mM L-threonyl-L-glutamine was produced in the case of using L-threonine methyl ester, 0.23 mM L-glutaminyl-L-glutamine was produced in the case of using L-glutamine methyl ester, 1.24 mM L-tyrosyl-L-glutamine was produced in the case of using L-tyrosine methyl ester, 6.52 mM L-arginyl-L-glutamine was produced in the case of using L-arginine methyl ester, and 8.22 mM L-aspartyl-α-L-glutamine was produced in the case of using L-aspartic acid-α-methyl ester. In addition, peptides composed of the corresponding amino acids and L-glutamines were also confirmed to be produced in the case of using L-leucine methyl ester, L-asparagine methyl ester, L-lysine methyl ester, L-aspartic acid-β-methyl ester, L-aspartic acid-α,β-dimethyl ester or L-glutamic acid-γ-methyl ester as the amino acid methyl ester (determination of quantity of these was not performed since no standard preparation was available).

(3) Measurement of Proline Iminopeptidase (pepI) Activity

The reaction was carried out at 30° C. using a reaction liquid (composition; 50 mM borate buffer (pH 9.0), 5 mM EDTA, 1 mM proline 2-naphthyl amide (proline-pNA). The liberation rate of naphthyl amide was measured as an increase in optical absorbance at 405 nanometers (nm) ($\epsilon$=9.83). The activity resulting in release of 1 μM of naphthyl amide in 1 minute was defined as 1 unit.

The proline iminopeptidase activity of the purified enzyme was $5.83 \times 10^3$ U/mg.

Example 9

Isolation of Proline Iminopeptidase (pepI) Gene from *Pseudomonas putida* Strain ATCC 12633 and Expression in *Escherichia coli*

1. Acquisition of Partial Fragment of Proline Iminopeptidase (pepI) Gene

A DNA was isolated from cultured cells of *Pseudomonas putida* strain ATCC 12633 using the same method as that in the section 3 of Example 7.

On the other hand, synthetic DNA oligomers (SEQ ID NO: 10: GGC GGA TCC GGT GCT CAA AGC GCA A and SEQ ID NO: 11: GGC GGA TC AGG TCG CCG CGT TCT TC) were produced based on the partial base sequence (AF032970) of proline iminopeptidase of *Pseudomonas putida* strain ATCC 12633 published in Genbank, and a partial gene fragment was amplified by PCR with TaKaRa LA (manufactured by Takara Shuzo) using these as primers.

2. Cloning Whole Length of Proline Iminopeptidase Gene from Gene Library

In order to acquire the whole length of proline iminopeptidase (pepI) gene of *Pseudomonas putida* strain ATCC 12633, Southern hybridization was first carried out in the same manner as described in part 5 of Example 7 using the partial fragment as a probe. As a result, a band was detected at about the 2.8 kb position in the XhoI cleaved product. Next, this 2.8 kb region fragment was collected and coupled to the SalI site of pUC18 to produce a library (100 strains) with *Escherichia coli* JM109. Colony hybridization was then carried out in the same manner as the Example and one positive clone was selected.

3. Base Sequence of Proline Iminopeptidase Gene of *Pseudomonas putida* Strain ATCC 12633

Plasmids possessed by the selected transformant were prepared in accordance with the method described in Molecular Cloning, 2nd edition, Cold Spring Harbor Press (1989), and the base sequence of a portion where hybridization with the probe occurred and nearby was determined. An open reading frame (ORF) was present that encoded a protein consisting of 337 amino acids, and it was verified that the whole length of this gene was acquired. The base sequence of the whole length of proline iminopeptidase gene is shown in SEQ ID NO: 14 of the Sequence Listing.

Note that the resulting ORF exhibited a base sequence homology of 46.3% with known proline iminopeptidase derived from *Corynebacterium* species bacteria, and exhibited a homology of 82.4% with proline iminopeptidase of *Pseudomonas putida* PA01.

4. Expression of Proline Iminopeptidase Gene in *Escherichia coli*

Plasmid pUCPPPEPI coupled to proline iminopeptidase (pepI) downstream of the lac promoter of pUC18 was constructed in order to express pepI in *Escherichia coli*. Fragments amplified by PCR using a chromosomal DNA as a template and the oligonucleotides shown in SEQ ID NOs: 9 and 11 (SEQ ID NO: 9: GGC GGA TCC GGT GCT CAA AGC GCA A; SEQ ID NO: 11: CAC GCG CTG CAG CAA ACC CCT CAT) as primers were treated, and after ligating with the cleaved products of pUC18, were used to transform *Escherichia coli* JM109. Strains having the target plasmid were selected from ampicillin-resistant strains, and the constructed expression plasmid was designated as pUCPPPEPI.

The *Escherichia coli* transformant having pUCPPPEPI was pre-cultured for 16 hours at 37° C. in an LB medium containing 0.1 mg/ml ampicillin. 1 mL of this pre-culture broth was inoculated into a 500 mL Sakaguchi flask containing 50 mL of LB medium followed by main culturing at 37° C. Two hours after the start of culturing, isopropyl-1-thio-β-D-galactopyranoside (IPTG) was added to a final concentration of 1 mM, followed by additional culturing for 3 hours.

After completion of the culturing, the microbes were collected and washed, suspended in 10 mL of 20 mM phosphate buffer (pH 8.0), and then subjected to ultrasonic crushing for 30 minutes at 180 W. The solution was collected and centrifuged at 12,000 g×10 minutes, and the resulting supernatant was used as a cell-free extract. As a result, proline iminopeptidase activity ($1.21 \times 10^3$ U/mg) was detected only in the case where pUCPPPEPI was introduced, and as a result, it was verified that the cloned pepI gene had been expressed in *Escherichia coli*.

Example 10

Synthesis of L-Alanyl-L-Glutamine by Proline Iminopeptidase of *Pseudomonas putida* Strain ATCC 12633

1. Detection of L-Alanyl-L-Glutamine-Forming Activity in *Pseudomonas putida* Strain ATCC 12633

*Pseudomonas putida* strain ATCC 12633 was liquid cultured overnight at 30° C. in an L medium to obtain microbial cells. The acquired microbial cells were suspended in 0.1 M borate buffer (pH 9.0), 10 mM EDTA, and the resulting suspension was used as an enzyme liquid. Note that determination of L-alanyl-L-glutamine-forming activity was carried out according to the enzyme activity measurement method described below. An enzyme reaction was carried out at 30° C. in a reaction solution composed of borate buffer (pH 9.0) at a final concentration of 0.1 M, EDTA at 10 mM, L-alanine methyl ester hydrochloride at 100 mM and L-glutamine at 150 mM, and the amount of L-alanyl-L-glutamine produced accompanying the reaction was determined by HPLC. The activity that produces 1 µM of L-alanyl-L-glutamine in 1 minute was defined as 1 unit.

L-alanyl-L-glutamine-forming activity of 0.051 unit per 1 mL of culture liquid was detected.

2. Synthesis of L-Alanyl-L-Glutamine by *Escherichia coli* Expressing Proline Iminopeptidase L-alanyl-L-glutamine-forming activity was measured using the aforementioned cell-free extract. As a result, an L-alanyl-L-glutamine-forming activity of 7.88 U/mg was detected in the case of introducing pUCPPPEPI, and it was verified that the cloned pepI gene was L-alanyl-L-glutamine-forming enzyme gene. The maximum accumulation of L-alanyl-L-glutamine was 25 mM.

Example 11

Isolation of Proline Iminopeptidase (pepI) Gene from *Pseudomonas putida* Strain FERM BP-8123 and Expression in *Escherichia coli*

1. Acquisition of Proline Iminopeptidase (pepI) Gene Section

A DNA was isolated from cultured cells (50 mL culture) of *Pseudomonas putida* strain FERM BP-8123 using the same method as Example 1 to acquire proline iminopeptidase (pepI) from *Pseudomonas putida* strain FERM BP-8123.

On the other hand, Southern hybridization was first carried out in the same manner as that described in the section 5 of Example 9 using the partial fragment of pepI gene of *Pseudomonas putida* strain ATCC 12633 amplified in Example 9 as a probe. As a result, a band was detected at about the 6.5 kb position in the PstI cleaved product.

This 6.5 kb region fragment was collected and coupled to the PstI site of pUC18 to produce a library (200 strains) with *Escherichia coli* JM109. Colony hybridization was then carried out in the same manner as the example and two positive clones were selected.

2. Base Sequence of Proline Iminopeptidase Gene of *Pseudomonas putida* strain FERM BP-8123

Plasmids retained by the selected transformants were prepared in accordance with the method described in Molecular Cloning, 2nd edition, Cold Spring Harbor Press (1989), and the base sequence of the position where hybridization with the probe occurred and nearby was determined. An open reading frame (ORF) was present that encoded protein consisting of 323 amino acids, so that it was verified that the whole length of this gene had been acquired. The base sequence of the whole length of proline iminopeptidase gene is shown in SEQ ID NO: 16 of the Sequence Listing. The resulting ORF exhibited a base sequence homology of 83% and an amino acid homology of 85% with the proline iminopeptidase of *Pseudomonas putida* strain ATCC 12633.

3. Expression of Proline Iminopeptidase Gene in *Escherichia coli*

A plasmid coupled to pepI gene downstream of the lac promoter of pUC18 was constructed in order to express pepI gene in *Escherichia coli*. Fragments amplified by PCR using a chromosomal DNA as a template and the oligonucleotides shown in SEQ ID NOs: 12 and 13 (SEQ ID NO: 12: CCC GAA TTC TTA CGG AGC GCG CAA TG; SEQ ID NO: 13: CGG GGA TCC CTT CAT GCT TCT TCA GG) as primers were treated, and after ligating with the cleaved products of pUC18, were used to transform *Escherichia coli* JM109. Strains having the target plasmids were selected from ampicillin-resistant strains, and the constructed expression plasmid was designated as pUCPGPEPI.

The *Escherichia coli* transformant having pUCPGPEPI was used to produce a cell-free extract using the same method as that in Example 8, and when proline iminopeptidase activity was measured, activity ($3.48 \times 10^1$ U/mg) was detected, so that it was verified that the cloned pepI gene had been expressed in *Escherichia coli*.

Example 12

Synthesis of L-Alanyl-L-Glutamine by Proline Iminopeptidase of *Pseudomonas putida* strain FERM BP-8123

1. Detection of L-Alanyl-L-Glutamine-Forming Activity in *Pseudomonas putida* Strain FERM BP-8123

Enzyme activity was measured by culturing *Pseudomonas putida* strain FERM BP-8123 in the same manner as that in Example 10. L-alanyl-L-glutamine-forming activity of 0.054 unit per 1 mL of culture liquid was detected.

2. Detection of L-Alanyl-L-Glutamine-Forming Enzyme Activity

L-alanyl-L-glutamine-forming activity was measured using a cell-free extract of *Escherichia coli* transformant retaining pUCPGPEPI. As a result, an L-alanyl-L-glutamine-forming activity of 0.470 U/mg was detected in the case of introducing pUCPGPEPI, so that it was verified that the cloned pepI gene was L-alanyl-L-glutamine-forming enzyme gene. The maximum accumulation of L-alanyl-L-glutamine was 30 mM.

Example 13

Synthesis of L-Alanyl-L-Glutamine by Enzyme Having Proline Iminopeptidase Activity of *Bacillus coagulans* Strain EK01

L-alanyl-L-glutamine-forming activity was measured according to the method disclosed in Example 10 using purified enzyme ($3.93 \times 10^5$ U/mg) from *Bacillus coagulans* strain EK01 commercially available from Toyobo Co., Ltd. As a result, an activity of 52.0 U/mg was detected, so that it was verified that this proline iminopeptidase is an enzyme having L-alanyl-L-glutamine-forming activity. The maximum accumulation of L-alanyl-L-glutamine was 18 mM.

Example 14

Effect of Inhibitors on Acquired Enzyme Activity

The effects of inhibitors on acquired proline iminopeptidase were investigated. The enzyme reaction was carried out for 30 minutes at 30° C. with a reaction solution consisting of 0.1 M borate buffer (pH 9.0), 10 mM EDTA, 100 mM L-alanine methyl ester hydrochloride, 150 mM L-glutamine and 1 mM inhibitor, followed by measurement of L-alanyl-L-glutamine synthesis. Enzyme activity was nearly completely inhibited when NEM (N-ethylmaleimide) was added at 1 mM for *Bacillus coagulans* strain EK01, *Pseudomonas putida* strain ATCC 12633, and *Pseudomonas putida* strain FERM BP-8123. In addition, the activities were also decreased to certain extents after the addition of IAA (iodoacetoamide) at 1 mM. On the other hand, the addition of PMSF (phenyl methyl sulfonyl fluoride) at 1 mM did not have an effect on the enzyme activity. The activity was not affected by any of the inhibitors investigated for *Corynebacterium glutamicum* strain ATCC 13286.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

INDUSTRIAL APPLICABILITY

According to the dipeptide production method of the present invention, a dipeptide can be produced using an L-amino acid ester and an L-amino acid that can be acquired inexpensively without going through a complex synthesis method, making it possible to reduce the production cost of dipeptides useful as pharmaceutical materials, functional foods and so forth. In addition, according to the dipeptide production method of the present invention, various types of dipeptides can be produced using various types of L-amino acid esters and L-amino acids as raw materials.

[Sequence Listing Free Text]
SEQ ID NO: 1: N-terminal amino acid sequence of a peptide-forming enzyme derived from *Corynebacterium glutamicum*
SEQ ID NO: 2: PCR primer
SEQ ID NO: 3: PCR primer
SEQ ID NO: 4: Code sequence of a peptide-forming enzyme derived from *Corynebacterium glutamicum*
SEQ ID NO: 5: Amino acid sequence of a peptide-forming enzyme derived from *Corynebacterium glutamicum*
SEQ ID NO: 6: Primer
SEQ ID NO: 7: Primer
SEQ ID NO: 8: Primer
SEQ ID NO: 9: Primer
SEQ ID NO: 10: Primer
SEQ ID NO 11: Primer
SEQ ID NO: 12: Primer
SEQ ID NO: 13: Primer
SEQ ID NO: 14: Code sequence of a peptide-forming enzyme derived from *Pseudomonas putida* ATCC 12633
SEQ ID NO: 15: Amino acid sequence of a peptide-forming enzyme derived from *Pseudomonas putida* ATCC 12633
SEQ ID NO: 16: Code sequence of a peptide-forming enzyme derived from *Pseudomonas putida* FERM BP-8123
SEQ ID NO: 17: Amino acid sequence of a peptide-forming enzyme derived from *Pseudomonas putida* FERM BP-8123

The invention claimed is:

1. A method for producing a dipeptide, comprising:
allowing a protein having proline iminopeptidase activity to act on an L-amino acid ester and an L-amino acid to form the dipeptide,
wherein said protein is selected from the group consisting of (A) and (B):
(A) a protein comprising the amino acid sequence of SEQ ID NO: 5,
(B) a protein comprising an amino acid sequence that includes substitution, deletion, insertion or addition of one to ten of amino acid(s) in the amino acid sequence of SEQ ID NO: 5, and has activity to produce a dipeptide from an L-amino acid ester and an L-amino acid,
wherein said L-amino acid ester is one or more members selected from the group consisting of an L-alanine ester, a glycine ester, and L-valine ester, an L-isoleucine ester, an L-methionine ester, an L-phyenylalanine ester, an L-serine ester, an L-threonine ester, an L-glutamine ester, an L-tyrosine ester, an L-arginine ester, an L-aspartic acid-α-ester, an L-aspartic acid-β-ester, an L-leucine ester, an L-asparagine ester, an L-lysine ester, an L-aspartic-α,β-dimethyl ester and L-glutamine-γ-ester.

2. The method for producing a dipeptide according to claim 1, wherein the protein having proline iminopeptidase activity is derived from a microbe belonging to genus *Corynebacterium*.

3. The method for producing a dipeptide according to claim 1, wherein the protein having proline iminopeptidase activity is derived from *Corynebacterium glutamicum*.

4. The method for producing a dipeptide according to claim 1, wherein the L-amino acid is one or more members selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

5. The method for producing a dipeptide according to claim 2, wherein the L-amino acid is one or more members selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

6. The method for producing a dipeptide according to claim 3, wherein the L-amino acid is one or more members selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

7. The method for producing a dipeptide according to claim 1, wherein said protein is a protein comprising the amino acid sequence of SEQ ID NO: 5.

8. The method for producing a dipeptide according to claim 1, wherein said protein is a protein consisting of the amino acid sequence of SEQ ID NO: 5.

9. The method for producing a dipeptide according to claim 1, wherein said protein is (B).

10. A method for producing a dipeptide comprising:
allowing a protein having proline iminopeptidase activity to act on an L-amino acid ester and an L-amino acid to form the dipeptide,
wherein said L-amino acid ester is one or more members selected from the group consisting of an L-alanine ester, a glycine ester, an L-valine ester, an L-isoleucine ester, an L-methionine ester, an L-phenylalanine ester, an L-serine ester, an L-threonine ester, an L-glutamine ester, an L-tyrosine ester, an L-arginine ester, an L-aspartic acid-α-ester, an L-aspartic acid-β-ester, an L-leucine ester, an L-asparagine ester, an L-lysine ester, an L-aspartic-α,β-dimethyl ester an L-glutamine-γ-ester, and
wherein said protein is produced by recombinant expression from a host cell transformed with DNA selected from the group consisting of (a) and (b):
(a) the DNA comprising nucleotides 57 to 1295 in the nucleotide sequence of SEQ ID NO: 4,
(b) a DNA that hybridizes under stringent conditions with the DNA comprising nucleotides 57 to 1295 in the nucleotide sequence of SEQ ID NO: 4, wherein said stringent conditions comprises 0.1×SSC, 0.1% SDS at 65° C., and encodes a protein having activity to form a dipeptide from an L-amino acid ester and an L-amino acid.

11. The method for producing a dipeptide according to claim 10, wherein the L-amino acid is one or more members selected from the group consisting of L-glutamine, L-asparagine, glycine, L-alanine, L-leucine, L-methionine, L-proline, L-phenylalanine, L-tryptophan, L-serine, L-threonine, L-tyrosine, L-lysine, L-arginine, L-histidine and L-glutamate.

12. The method for producing a dipeptide according to claim 10, wherein the DNA is (a).

13. The method for producing a dipeptide according to claim 10, wherein the DNA is (b).

* * * * *